(12) United States Patent
Bringe et al.

(10) Patent No.: US 7,541,329 B2
(45) Date of Patent: Jun. 2, 2009

(54) OIL BODY ASSOCIATED PROTEIN COMPOSITIONS AND METHODS OF USE THEREOF FOR REDUCING THE RISK OF CARDIOVASCULAR DISEASE

(75) Inventors: Neal A. Bringe, St. Charles, MO (US); Kanthasamy Karunanandaa, Creve Coeur, MO (US)

(73) Assignee: Monsanto Technology LLC, St. Louis, MO (US)

( * ) Notice: Subject to any disclaimer, the term of this patent is extended or adjusted under 35 U.S.C. 154(b) by 399 days.

(21) Appl. No.: 10/511,669

(22) PCT Filed: Apr. 17, 2003

(86) PCT No.: PCT/US03/12009

§ 371 (c)(1),
(2), (4) Date: May 23, 2005

(87) PCT Pub. No.: WO03/088749

PCT Pub. Date: Oct. 30, 2003

(65) Prior Publication Data

US 2005/0214346 A1    Sep. 29, 2005

Related U.S. Application Data

(60) Provisional application No. 60/373,460, filed on Apr. 18, 2002.

(51) Int. Cl.
*A61K 38/00* (2006.01)
*A61K 33/00* (2006.01)
*C07K 14/00* (2006.01)

(52) U.S. Cl. .................. 514/2; 424/757; 424/656; 424/634; 530/300; 530/370; 530/377; 530/378

(58) Field of Classification Search .................. 514/2; 424/757, 656, 634; 530/300, 370, 377, 378
See application file for complete search history.

(56) References Cited

U.S. PATENT DOCUMENTS

| | | | | |
|---|---|---|---|---|
| 3,642,490 | A | 2/1972 | Hawley et al. | 99/17 |
| 3,694,221 | A | 9/1972 | Hoer et al. | 99/17 |
| 4,360,537 | A | 11/1982 | Tan et al. | 426/656 |
| 5,478,585 | A | 12/1995 | Isono et al. | 426/417 |
| 5,559,220 | A | 9/1996 | Roessler et al. | 536/23.6 |
| 5,830,887 | A * | 11/1998 | Kelly | 514/182 |
| 5,855,892 | A | 1/1999 | Potter | 424/757 |
| 5,968,516 | A * | 10/1999 | Liu | 424/757 |
| 6,136,367 | A | 10/2000 | Hoie | 424/757 |
| 6,171,640 | B1 | 1/2001 | Bringe | 426/656 |
| 2004/0014640 | A1 * | 1/2004 | Kohno et al. | 514/2 |

FOREIGN PATENT DOCUMENTS

| | | |
|---|---|---|
| CN | 86105538 | 7/1986 |
| EP | 0 533 512 | 8/2002 |
| EP | 1 323 425 A1 * | 7/2003 |
| JP | 2001-114800 | 4/2001 |
| JP | 2002-101820 | 4/2002 |
| WO | WO 89/01495 | 2/1989 |
| WO | WO 00/30602 | 6/2000 |
| WO | WO 00/30663 | 6/2000 |
| WO | WO 01/36648 | 5/2001 |
| WO | WO 02/26243 A1 * | 4/2002 |
| WO | WO 02/26788 | 4/2002 |

OTHER PUBLICATIONS

M.C. Berenbaum, Synergy, additivism and antagonism in immunosuppression, A critical review, Clin. Exp. Immunol, 1977, vol. 28, pp. 1-18.*
M.C. Berenbaum, What is Synergy?, Pharmacological Reviews, 1989, vol. 1969, vol. 41, pp. 93-141.*
Yamada, et al, Increased clearance of plasma cholesterol after injection of apolipoprotein E into Watanabe heritable hyperlipidemic rabbits, Proc. Natl. Acad. Sci. USA, Jan. 1989, vol. 86, pp. 665-669.*
Hori, et al., Soy Protein Hydrolyzate with Bound Phospholipids Reduces Serum Cholesterol Levels in Hypercholesterolemic Adult Male Volunteers, Boisci. Biotechnol. Biochem., 2001, 65(1), pp. 72-78.*
Lovati, et al/Manzoni, et al, Soybean Protein Products as Regulators of Liver Low-Density Lipoprotein Receptors I Identification of Active Beta-Conglycinin Subunits II Alpha and Alpha' Rich Commerical Soy Concentrate and Alpha' Deficient Mutant Differently Affect Low-Density Lipoprotein Activation, J Agric Food Chem., 1998, V 46, pp. 2474-2484.*
M. Fiordaliso, et al., Dietary Oligofructose Lower Triglycerides, Phospholipids and Cholesterol in Serum and Very Low Density Lipoproteins of Rats, Lipids, 1995, vol. 30 No. 2, pp. 163-167.*
J. Wojcicki, et al., Clinical Evaluation of Lecithin as a Lipid-lowering Agent, Phytotherapy Research, Dec. 1995, vol. 9, Iss. 8, pp. 597-599.*
Tallarida, Ronald J., "Drug Synergism and Dose Effect Data Analysis", (2000) Chapman & Hall/CRC, title page and table of contents provided.*

(Continued)

*Primary Examiner*—Jon P Weber
*Assistant Examiner*—Abdel A Mohamed
(74) *Attorney, Agent, or Firm*—Chunping Li, Esq.; Sonnenschein Nath & Rosenthal LLP

(57) ABSTRACT

Compositions and methods for reducing hypercholesterolemia and, accordingly, the risk of cardiovascular disease, are provided. Such compositions may comprise isolated oil body associated proteins. Additionally provided are foodstuffs to which one or more oil body associated proteins have been added. The compositions employed in the invention may further comprise additive compounds, for example, a saponin, an isoflavone, a phospholipid, a carbohydrate substantially resistant to digestion, or a combination thereof. The methods and compositions of the invention may be used to lower cholesterol and other lipid levels in subjects to achieve a reduction in the risk of cardiovascular disease.

34 Claims, 9 Drawing Sheets

OTHER PUBLICATIONS

Abell, "Targeting and topology of seed oleosins," Ph.D. Dissertation, Department of Biological Sciences, Calgary, Alberta, Canada, May, 1999.
Anderson et al., "Meta-analysis of the effects of soy protein intake on serum lipids," *N Engl J Med*, 333(5):276-282, 1995.
Anthony et al., "Neither isoflavones nor the alcohol-extracted fraction added to alcohol-washed soy protein isolate restores the lipoprotein effects of soy protein isolate," 4th *International Symposium on the Role of Soy Preventing and Treating Chronic Disease*, p. 35, San Diego, CA, Nov. 4-7, 2001.
Bringe and Cheng, "Low-fat, low-cholesterol egg yolk in food applications," *Food Tech*, 49(5):94-106, 1995.
Bringe, , "Properties of low-fat, low cholesterol egg yolk prepared by supercritical CO2 extraction," *Adv Exp Med Biol*, 415:161-181, 1997.
Clarkson et al., "A paradoxial association between plasma isoflavone concentrations on a soy-containing diet, and both plasma lipoproteins and atherosclerosis," 4th *International Symposium on the Role of Soy Preventing and Treating Chronic Disease*, p. 35, San Diego, CA, Nov. 4-7, 2001.
Forsythe et al., "Dietary protein effects on cholesterol and lipoprotein concentrations: a review," *J Am Coll Nutr*, 5:533-549, 1986.
Fransen et al., "Oil bodies and their associated proteins, oleosin and caleosin," *Plysiol Plant*, 112(3):301-307, 2001.
GenBank Accession No. AAA67699.
GenBank Accession No. AAA68065.
GenBank Accession No. AAA68066.
GenBank Accession No. CAA55348.
GenBank Accession No. P29530.
GenBank Accession No. P29531.
Hori et al., "Cholesterol-lowering effects of isolated soybean protein hydrolyzate with bound phospholipids in rats," *J Jpn Soc Nutr Food Sci*, 52:135-145, 1999.
Hori et al., "Soy protetin hydrolyzate with bound phospholipids reduces serum cholesterol levels in hypercholesterolemic adult male volunteers," *Biosci Biotechnol Biochem*, 65(1):72-78, 2001.
Huang, "Oleosins and oil bodies in seeds and other organs," *Plant Physiol*, 110:1055-1061, 1996.
Iwami et al., "Characterization of a major bile acid-binding peptide from the peptic-pancreatic digest of soybean protein," *Soy Protein Res Com Japan*, 15:74-80, 1994.
Iwami et al., "Molecular recognition of bile acids by soy protein and modeling of its mimetics," *English Title of the S.P.R.C. Report* vol. 22, abstract from *Soy Protein Research*, Japan, 4:58-64, 2001.
Kanamoto et al., "Soybean 'resistant protein' that prevents colon and liver carcinogenesis induced by bile acids in rat," 4th *International Symposium on the Role of Soy Preventing and Treating Chronic Disease*, A-13, p. 42, San Diego, CA, Nov. 4-7, 2001.
Keenan, "Milk lipid globules and their surrounding membrane: a brief history and perspectives for future research," J Mammary Gland Biol Neopasia, 6(3):365-371, 2001.
Leber et al., *Yeast*, 10:1421-1428, 1994.
Lovati et al., "Soy protein peptides regulate cholesterol homeostasis in Hep G2 cells," J Nutr, 130:2543-2549, 2000.
Morita et al., "Resistant proteins alter cecal short-chain fatty acid profiles in rats fed high amylose cornstarch," *J Nutr*, 128:1156-1164, 1998.
Murphy et al., "A class of amphipathic proteins associated with lipid storage bodies in plants. Possible similarities with animal serum apolipoproteins," *Biochim Biophys Acta*, , 1088:86-94, 1991.
Nagaoka et al., "Identification of novel hypocholesterolemic peptides derived from bovine milk beta-lactoglobulin," *Biochem Biophys Res Comm*, 281:11-17, 2001.
Nagaoka et al., "Soy protein peptic hydrolysate with bound phospholipids decreases micellar solubility and cholesterol absorption in rats and caco-2 cells," *J Nutr*, 129:1725-1730, 1999.
Oakenfull, "Soy proteins, saponins and plasma cholesterol," Letter to the Editor, *J Nutr*, 131:2971-2972, 2001.
Pieper-Fürst et al., "Purification and characterization of a 14-kilodalton protein that is bound to the surface of polyhydroxyalkanoic acid granules in *Rhodococcus ruber*," *J Bacteriol*, 176:4328-4337, 1994.
Potter, "Soy-new health benefits associated with an ancient food," Nutrition Today, 35(2):53-60, 2000.
Roessler, J Phycol, "Effects of silicon deficiency on lipid composition and metabolism in the diatom cyclotella cryptica," (London), 24:394-400, 1988.
Samoto et al., "Improvement of the off-flavor of soy protein isolate by removing oil-body associated proteins and polar lipids," *Biosci Biotechnol Biochem*, 62(5):935-940, 1998.
Sitori et al., "Reduction of serum cholesterol by soy proteins: clinical experience and potential molecular mechanisms," *Nutr Metab Cardiovasc Dis*, 8:334-340, 1998.
Sugano et al., "The hypocholesterolemic action of the undigested fraction of soybean protein in rats," *Atherosclerosis*, 72:115-122, 1988.
Ting et al., "Oleosin of plant seed oil bodies is correctly targeted to the lipid bodies in transformed yeast," *J. Biol. Chem.*, 272(6):3699-3706, 1997.
Tzen and Huang, "Surface structure and properties of plant seed oil bodies," *J. Cell Biol*, 117:327-335, 1992.
Utsumi et al., In: *Food Proteins and Their Applications*, Damodaran and Paraf (eds.), Marcel Dekker, Inc., NY, 1997.
Wu et al., "Genomic cloning of 18 kDa oleosin and detection of triacylglycerols and oleosin isoforms in maturing rice and postgerminative seedlings," *J. Biochem*, 123:386-391, 1998.
Yoshikawa et al., "Study on a low molecular weight peptide derived from soybean protein having hypocholesteremic activity," *Soy Protein Research*, Japan, 2:125-128, 1999.
Zweytick et al., "Intracellular lipid particles of eukaryotic cells," *Biochim Biophys Acta*, , 1469:101-120, 2000.
Kambara et al., "Effects of soybean b-conglycin on serum high triacylglycerol level lowering and bmi in human subjects and study of long-term and large intake of soybean b-conglycin on clinical parameters," *J of Nutritional Food*, 7:1-19, 2004.
GenBank Accession No. AAA67699, 1995.
GenBank Accession No. AAA68065, 1995.
GenBank Accession No. AAA68066, 1995.
GenBank Accession No. CAA55348, 1995.
GenBank Accession No. P29530, 2000.
GenBank Accession No. P29531, 2000.
Kalinski et al., "Molecular cloning of protein associated with soybean seed oil bodies that is similar to thiol proteases of the papain family," *J. of Biol. Chem.*, 265(23) 13843-13848, 1990.

\* cited by examiner mttqvpphsv qvhtttthry eagvvppgar fetsyeagvk aasiyhserg
pttsqvlavl aglpvggill llagltlagt ltglavatpl fvlfspvlvp
atvaiglava gfltsgafgl talssfswil nyiretqpas enlaaaakhh
laeaaeyvgq ktkevgqktk evgqdiqska qdtreaaard areaaardar
eaaardakve ardvkrttvt attata

FIG. 1 mttvpphsvq vhttthryea gvvpparfea pryeagikap ssiyhsergp
ttsqvlavva glpvggilll lagltlagtl tglvvatplf iifspvlipa
tvaiglavag fltsgvfglt alssfswiln yiretqpase nlaaaakhhl
aeaaeyvgqk tkevgqktke vgqdiqskaq dtreaaarda rdareaaard
ardakveard vkrttvtatt ata

FIG. 2

MADRDRSGIYGGGAYGQQQGRPPMGEQVKGMIHDKGPTASQALTVATLFPLGGLLLVLSG
LALAASTVGLAVATPVFLLFSPVLVPAALLIGTAVAGFLTSGALGLGGLSSLTCLANTAR
QAFQRTPDYVEEARRRMAEAAAHAGHKTAQAGHGIQSKAQEAGAGTGAGGGRTSS

FIG. 3

MADHHRGATGGGGGYGDLQRGGGMHGEAQQQQKQGAMMTALKAATAATFGGSMLVLSGLI
LAGTVIALTVATPVLVIFSPVLVPAAIALALMAAGFVTSGGLGVAALSVFSWMYKYLTGK
HPPAADQLDHAKARLASKARDVKDAAQHRIDQAQGS

FIG. 4

MADRDRSGIYGGAHATYGQQQQQGGGGRPMGEQVKKGMLHDKGPTASQALTVATLFPLGG
LLLVLSGLALTASVVGLAVATPVFLIFSPVLVPAALLIGTAVMGFLTSGALGLGGLSSLT
CLANTARQAFQRTPDYVEEARRRMAEAAAQAGHKTAQAGQAIQGRAQEAGTGGGAGAGAG
GGGRASS

FIG. 5

MATTTYDRHHVTTTQPQYRHDQHTGDRLTHPQRHEQGPSTGKIMVIMALLPITGILFGLA
GITSSDGYRASLATPLFVIFSPVIVPAMIAIGLAVTGFLTSGTFGLTGLSSLSYLFNMVR
RSTMSVPDQMDYVKGKLQDVGEYTGQKTKDLGQKIQHTAHEMGDQGQGQGQGGGKEGRKE
GGK

FIG. 6

SEQUENCE LISTING

<160> NUMBER OF SEQ ID NOS: 18

<210> SEQ ID NO 1
<211> LENGTH: 35
<212> TYPE: PRT

```
<213> ORGANISM: Artificial Sequence
<220> FEATURE:
<223> OTHER INFORMATION: Description of Artificial Sequence:  Synthetic
      Peptide

<400> SEQUENCE: 1

Val Phe Asp Gly Glu Leu Gln Glu Gly Arg Val Leu Ile Val Pro Gln
 1               5                  10                  15

Asn Phe Val Val Ala Ala Arg Ser Gln Ser Asp Asn Phe Glu Tyr Val
                20                  25                  30

Ser Phe Lys
         35

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Leu Arg Met Ile Thr Leu Ala Ile Pro Val Asn Lys Pro Gly Arg Phe
 1               5                  10                  15

Glu Ser Phe Phe Leu
                20

<210> SEQ ID NO 3
<211> LENGTH: 25
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Ile Phe Val Ile Pro Ala Gly Tyr Pro Val Val Val Asn Ala Thr Ser
 1               5                  10                  15

His Leu Asn Phe Phe Ala Ile Gly Ile
                20                  25

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Leu Gln Glu Ser Val Ile Val Glu Ile Ser Lys Lys
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Gln Gln Gln Glu Glu Gln Pro Leu Glu Val Arg Lys
 1               5                  10
```

```
<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Asn Gln Tyr Gly His Val Arg
 1               5

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Ala Ile Val Ile Leu Val Ile Asn Glu Gly Asp Ala Asn Ile Glu Leu
 1               5                  10                  15

Val Gly Leu

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Asn Ile Leu Glu Ala Ser Tyr Asp Thr Lys Phe Glu Glu Ile Asn Lys
 1               5                  10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Val Lys Phe Ile Thr Ala Ala Thr Ile Gly Ile Thr Leu Leu Leu Leu
 1               5                  10                  15

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Tyr Glu Thr Asn Ser Ser Leu Asn Asn Pro Pro Ser Arg
 1               5                  10

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide
```

<400> SEQUENCE: 11

Ile Phe Val Ile Pro Ala Gly Tyr Pro Val Val Asn Ala Thr Ser
1               5                   10                  15

Asp Leu Asn Phe Phe Ala Phe Gly Ile
            20                  25

<210> SEQ ID NO 12
<211> LENGTH: 226
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Met Thr Thr Gln Val Pro Pro His Ser Val Gln Val His Thr Thr Thr
1               5                   10                  15

Thr His Arg Tyr Glu Ala Gly Val Val Pro Pro Gly Ala Arg Phe Glu
            20                  25                  30

Thr Ser Tyr Glu Ala Gly Val Lys Ala Ala Ser Ile Tyr His Ser Glu
        35                  40                  45

Arg Gly Pro Thr Thr Ser Gln Val Leu Ala Val Leu Ala Gly Leu Pro
    50                  55                  60

Val Gly Gly Ile Leu Leu Leu Ala Gly Leu Thr Leu Ala Gly Thr
65                  70                  75                  80

Leu Thr Gly Leu Ala Val Ala Thr Pro Leu Phe Val Leu Phe Ser Pro
                85                  90                  95

Val Leu Val Pro Ala Thr Val Ala Ile Gly Leu Ala Val Ala Gly Phe
            100                 105                 110

Leu Thr Ser Gly Ala Phe Gly Leu Thr Ala Leu Ser Ser Phe Ser Trp
        115                 120                 125

Ile Leu Asn Tyr Ile Arg Glu Thr Gln Pro Ala Ser Glu Asn Leu Ala
    130                 135                 140

Ala Ala Ala Lys His His Leu Ala Glu Ala Ala Glu Tyr Val Gly Gln
145                 150                 155                 160

Lys Thr Lys Glu Val Gly Gln Lys Thr Lys Glu Val Gly Gln Asp Ile
                165                 170                 175

Gln Ser Lys Ala Gln Asp Thr Arg Glu Ala Ala Ala Arg Asp Ala Arg
            180                 185                 190

Glu Ala Ala Ala Arg Asp Ala Arg Glu Ala Ala Ala Arg Asp Ala Lys
        195                 200                 205

Val Glu Ala Arg Asp Val Lys Arg Thr Val Thr Ala Thr Thr Ala
    210                 215                 220

Thr Ala
225

<210> SEQ ID NO 13
<211> LENGTH: 223
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Met Thr Thr Val Pro Pro His Ser Val Gln Val His Thr Thr Thr His
1               5                   10                  15

```
Arg Tyr Glu Ala Gly Val Val Pro Pro Ala Arg Phe Glu Ala Pro Arg
             20                  25                  30

Tyr Glu Ala Gly Ile Lys Ala Pro Ser Ser Ile Tyr His Ser Glu Arg
         35                  40                  45

Gly Pro Thr Thr Ser Gln Val Leu Ala Val Val Ala Gly Leu Pro Val
     50                  55                  60

Gly Gly Ile Leu Leu Leu Ala Gly Leu Thr Leu Ala Gly Thr Leu
 65                  70                  75                  80

Thr Gly Leu Val Val Ala Thr Pro Leu Phe Ile Ile Phe Ser Pro Val
             85                  90                  95

Leu Ile Pro Ala Thr Val Ala Ile Gly Leu Ala Val Ala Gly Phe Leu
            100                 105                 110

Thr Ser Gly Val Phe Gly Leu Thr Ala Leu Ser Ser Phe Ser Trp Ile
        115                 120                 125

Leu Asn Tyr Ile Arg Glu Thr Gln Pro Ala Ser Glu Asn Leu Ala Ala
130                 135                 140

Ala Ala Lys His His Leu Ala Glu Ala Ala Glu Tyr Val Gly Gln Lys
145                 150                 155                 160

Thr Lys Glu Val Gly Gln Lys Thr Lys Glu Val Gly Gln Asp Ile Gln
                165                 170                 175

Ser Lys Ala Gln Asp Thr Arg Glu Ala Ala Ala Arg Asp Ala Arg Asp
            180                 185                 190

Ala Arg Glu Ala Ala Ala Arg Asp Ala Arg Asp Ala Lys Val Glu Ala
        195                 200                 205

Arg Asp Val Lys Arg Thr Thr Val Thr Ala Thr Thr Ala Thr Ala
    210                 215                 220

<210> SEQ ID NO 14
<211> LENGTH: 175
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 14

Met Ala Asp Arg Asp Arg Ser Gly Ile Tyr Gly Gly Gly Ala Tyr Gly
 1               5                  10                  15

Gln Gln Gln Gly Arg Pro Pro Met Gly Glu Gln Val Lys Gly Met Ile
             20                  25                  30

His Asp Lys Gly Pro Thr Ala Ser Gln Ala Leu Thr Val Ala Thr Leu
         35                  40                  45

Phe Pro Leu Gly Gly Leu Leu Leu Val Leu Ser Gly Leu Ala Leu Ala
     50                  55                  60

Ala Ser Thr Val Gly Leu Ala Val Ala Thr Pro Val Phe Leu Leu Phe
 65                  70                  75                  80

Ser Pro Val Leu Val Pro Ala Ala Leu Leu Ile Gly Thr Ala Val Ala
             85                  90                  95

Gly Phe Leu Thr Ser Gly Ala Leu Gly Leu Gly Gly Leu Ser Ser Leu
            100                 105                 110

Thr Cys Leu Ala Asn Thr Ala Arg Gln Ala Phe Gln Arg Thr Pro Asp
        115                 120                 125

Tyr Val Glu Glu Ala Arg Arg Arg Met Ala Glu Ala Ala His Ala
130                 135                 140

Gly His Lys Thr Ala Gln Ala Gly His Gly Ile Gln Ser Lys Ala Gln
145                 150                 155                 160
```

```
Glu Ala Gly Ala Gly Thr Gly Ala Gly Gly Arg Thr Ser Ser
            165                 170                 175
```

<210> SEQ ID NO 15
<211> LENGTH: 156
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

```
Met Ala Asp His His Arg Gly Ala Thr Gly Gly Gly Gly Tyr Gly
  1               5                  10                  15

Asp Leu Gln Arg Gly Gly Gly Met His Gly Glu Ala Gln Gln Gln
                 20                  25                  30

Lys Gln Gly Ala Met Met Thr Ala Leu Lys Ala Ala Thr Ala Thr
                 35                  40                  45

Phe Gly Gly Ser Met Leu Val Leu Ser Gly Leu Ile Leu Ala Gly Thr
     50                  55                  60

Val Ile Ala Leu Thr Val Ala Thr Pro Val Leu Val Ile Phe Ser Pro
 65                  70                  75                  80

Val Leu Val Pro Ala Ala Ile Ala Leu Ala Leu Met Ala Ala Gly Phe
                 85                  90                  95

Val Thr Ser Gly Gly Leu Gly Val Ala Ala Leu Ser Val Phe Ser Trp
                100                 105                 110

Met Tyr Lys Tyr Leu Thr Gly Lys His Pro Pro Ala Ala Asp Gln Leu
                115                 120                 125

Asp His Ala Lys Ala Arg Leu Ala Ser Lys Ala Arg Asp Val Lys Asp
                130                 135                 140

Ala Ala Gln His Arg Ile Asp Gln Ala Gln Gly Ser
145                 150                 155
```

<210> SEQ ID NO 16
<211> LENGTH: 187
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

```
Met Ala Asp Arg Asp Arg Ser Gly Ile Tyr Gly Gly Ala His Ala Thr
  1               5                  10                  15

Tyr Gly Gln Gln Gln Gln Gln Gly Gly Gly Gly Arg Pro Met Gly Glu
                 20                  25                  30

Gln Val Lys Lys Gly Met Leu His Asp Lys Gly Pro Thr Ala Ser Gln
                 35                  40                  45

Ala Leu Thr Val Ala Thr Leu Phe Pro Leu Gly Gly Leu Leu Leu Val
     50                  55                  60

Leu Ser Gly Leu Ala Leu Thr Ala Ser Val Val Gly Leu Ala Val Ala
 65                  70                  75                  80

Thr Pro Val Phe Leu Ile Phe Ser Pro Val Leu Val Pro Ala Ala Leu
                 85                  90                  95

Leu Ile Gly Thr Ala Val Met Gly Phe Leu Thr Ser Gly Ala Leu Gly
                100                 105                 110

Leu Gly Gly Leu Ser Ser Leu Thr Cys Leu Ala Asn Thr Ala Arg Gln
                115                 120                 125
```

```
Ala Phe Gln Arg Thr Pro Asp Tyr Val Glu Ala Arg Arg Arg Met
    130                 135                 140

Ala Glu Ala Ala Ala Gln Ala Gly His Lys Thr Ala Gln Ala Gly Gln
145                 150                 155                 160

Ala Ile Gln Gly Arg Ala Gln Glu Ala Gly Thr Gly Gly Gly Ala Gly
                165                 170                 175

Ala Gly Ala Gly Gly Gly Gly Arg Ala Ser Ser
            180                 185

<210> SEQ ID NO 17
<211> LENGTH: 183
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 17

Met Ala Thr Thr Thr Tyr Asp Arg His His Val Thr Thr Thr Gln Pro
1               5                   10                  15

Gln Tyr Arg His Asp Gln His Thr Gly Asp Arg Leu Thr His Pro Gln
                20                  25                  30

Arg His Glu Gln Gly Pro Ser Thr Gly Lys Ile Met Val Ile Met Ala
            35                  40                  45

Leu Leu Pro Ile Thr Gly Ile Leu Phe Gly Leu Ala Gly Ile Thr Ser
        50                  55                  60

Ser Asp Gly Tyr Arg Ala Ser Leu Ala Thr Pro Leu Phe Val Ile Phe
65                  70                  75                  80

Ser Pro Val Ile Val Pro Ala Met Ile Ala Ile Gly Leu Ala Val Thr
                85                  90                  95

Gly Phe Leu Thr Ser Gly Thr Phe Gly Leu Thr Gly Leu Ser Ser Leu
            100                 105                 110

Ser Tyr Leu Phe Asn Met Val Arg Arg Ser Thr Met Ser Val Pro Asp
        115                 120                 125

Gln Met Asp Tyr Val Lys Gly Lys Leu Gln Asp Val Gly Glu Tyr Thr
130                 135                 140

Gly Gln Lys Thr Lys Asp Leu Gly Gln Lys Ile Gln His Thr Ala His
145                 150                 155                 160

Glu Met Gly Asp Gln Gly Gln Gly Gln Gly Gln Gly Gly Lys Glu
                165                 170                 175

Gly Arg Lys Glu Gly Gly Lys
            180

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 18

Gln Asn Pro Ser His Asn Lys Cys Leu Arg
1               5                   10
```

OIL BODY ASSOCIATED PROTEIN COMPOSITIONS AND METHODS OF USE THEREOF FOR REDUCING THE RISK OF CARDIOVASCULAR DISEASE

This application is a national stage application under 35 U.S.C. §371 of International Application No. PCT/US03/12009 filed Apr. 17, 2003, which claims the priority of U.S. Provisional Patent Application Ser. No. 60/373,460, filed Apr. 18, 2002, the entire contents of which are specifically incorporated herein by reference.

FIELD OF THE INVENTION

The present invention relates to novel compositions, polypeptides and methods for reducing cholesterol levels and decreasing the risk of cardiovascular disease. More particularly, the invention relates to novel compositions comprising oil body associated proteins and use thereof for the prevention and treatment of elevated cholesterol and cardiovascular disease.

BACKGROUND OF THE INVENTION

Cardiovascular disease is a leading cause of morbidity and mortality within the human population. This is particularly so in the United States and in Western European countries. Numerous causative factors have been implicated in the development of cardiovascular disease. Several of these factors include hereditary predisposition to the disease, lifestyle factors such as smoking and diet, age, gender, hypertension, and hyperlipidemia, including hypercholesterolemia. A number of these factors, particularly hyperlipidemia and hypercholesteremia, contribute to the development of atherosclerosis, a primary cause of cardiovascular disease.

High blood cholesterol concentration is one of the major risk factors for cardiovascular disease in humans. Elevated low density lipoprotein cholesterol ("LDL") and total cholesterol are directly related to an increased risk of coronary heart disease. (Anderson et al., 1987). Although high levels of total cholesterol and LDL are risk factors in developing atherosclerosis and vascular diseases, a deficiency of high density lipoprotein cholesterol ("HDL") has recently been recognized as an additional risk factor for developing these conditions. Several clinical trials support the theory of a protective role of HDL against atherosclerosis. One such study has demonstrated that, in women, every 1-mg/dl increase in HDL in the blood decreases the risk for coronary vascular disease by 3%. (Gordon et al., 1989).

Studies have indicated that dietary changes can reduce cholesterol in humans. Of these, particular studies have indicated that the quality, as well as the quantity, of protein ingested greatly affects serum cholesterol levels. (Carol and Hamilton, 1975; Nagaoka et al., 1992; Potter, 1995). Ingestion of vegetable protein materials in place of animal protein in the diet is associated with a lower risk of cardiovascular disease, which may reflect decreases in serum cholesterol levels. Particularly, soy protein, a vegetable protein, has been shown to reduce serum cholesterol levels relative to the animal protein casein (Nagaoka et al., 1999). A more recent meta-analysis of the effects of soy protein intake on serum lipids in humans has shown that dietary soy protein is significantly related to lowering serum concentrations of total cholesterol and LDL in humans without significantly affecting HDL-holesterol concentrations (Anderson et al., 1995).

One of the agents responsible for the ability of soy protein to lower cholesterol is the high molecular weight fraction (HMF). The HMF constitutes the non-digestible portion of soy protein that remains intact after proteolytic digestion. This fraction, therefore, is composed of a number of different peptides or peptide fragments. The HMF of soy protein, in fact, has been shown to significantly reduce serum cholesterol in both animal and human studies. It is believed that the non-digestible HMF prevents the uptake of cholesterol either by the prevention of passive uptake of cholesterol by the brush border membrane or by the prevention of protein-mediated uptake of cholesterol. In contrast, the lower molecular weight fraction, a digestible fraction of soy protein, has actually been shown to increase serum cholesterol (Sugano, et al., 1988).

Despite the potential therapeutic value of soy protein, and in particular the HMF, as a cholesterol lowering agent, the specific constituents responsible for its non-digestive and hypocholesterolemic activity have not been determined. A need, therefore, remains to identify these active constituents in an effort to provide a therapeutic agent that is more potent in reducing cholesterol and other risk factors associated with cardiovascular disease.

SUMMARY OF THE INVENTION

In one aspect, the invention provides a method of preparing a foodstuff, comprising the steps of: (a) obtaining a selected foodstuff; and (b) adding isolated oil body associated protein to the foodstuff, wherein the consumption of an effective amount of the foodstuff decreases the serum cholesterol of a subject in need thereof. In certain embodiments, the method further comprises adding at least one compound selected from the group consisting of a saponin, a phytoestrogen, a phospholipid, and a carbohydrate substantially resistant to digestion. The oil body associated protein may comprise lipoproteins and/or oleosin. In one embodiment, the foodstuff is soy-based. The composition may lack or comprise oil body associated body protein prior to the step of adding. Examples of foodstuffs include, but are specifically not limited to, soy flour, soy grit, soy meal, soy flakes, soy milk powder, soy protein concentrate, soy protein isolate and isolated soy polypeptide. In certain embodiments of the invention, the soy protein isolate is a high molecular weight fraction of a soy material treated with a protease. In further embodiments, the isolated soy polypeptide comprises β-conglycinin, or a fragment thereof and/or is glycinin, or a fragment thereof.

In another aspect, the invention provides a composition for treating or preventing hypercholesterolemia comprising: (a) glycinin and/or β-conglycinin, or fragments thereof; and (b) oil body associated protein, wherein the glycinin and/or β-conglycinin and the oil body associated protein are present in an amount effective to provide a synergistic effect for the treatment or prevention of hypercholesterolemia in a subject in need thereof. In one embodiment, the glycinin or β-conglycinin is at least partially hydrolyzed by an enzyme or a mixture of enzymes. In further embodiments, the composition comprises glycinin, or fragments thereof, and purified oil body associated protein and in another embodiment it comprises β-conglycinin, or fragments thereof, and purified oil body associated protein. In certain embodiments of the invention, the composition may comprise from about 1% to about 5%, from about 5% to about 10%, greater than about 10%, or about 30% to about 50% oil body associated protein by weight.

A composition provided by the invention may further comprise at least one additive compound, including a saponin, a phytoestrogen, a phospholipid, and a carbohydrate substantially resistant to digestion. An example of phytoestrogen includes an isoflavone. Examples of isoflavones include genistein, diadzein, equol, biochanin A, formononetin, and their respective naturally occurring glucosides and glucoside conjugates. Examples of carbohydrate include high amylose starch, oligofructose, and soy cotyledon fiber. In one embodiment of the invention, the phospholipid is selected from the group consisting of lecithin, lyso-lecithin, and lecithin with a modified fatty acid composition. In further embodiments, the saponin is selected from the group consisting of soy saponin A, saponin B, saponin E, sapogenol A, sapogenol B, and sapogenol E. The oil body associated protein may comprise lipoprotein, including mammalian lipoprotein, egg yolk lipoprotein or fat globule membrane protein. The oil body associated protein may also be oleosin, including the low molecular weight fraction of oleosin.

In one embodiment of the invention, oil body associated protein comprises a polypeptide fragment containing an amphipathic sequence. Where the composition comprises glycinin, it may comprise the basic subunit of glycinin, including the B-1b subunit. The composition may also comprise β-conglycinin, including the α' subunit or a fragment thereof. The composition may be further defined as comprising more than 40% β-conglycinin or a fragment thereof. The composition may further be defined as comprising one or more polypeptide sequences selected from the group consisting of SEQ ID NO:1, SEQ ID NO:2, SEQ ID NO:3, SEQ ID NO:4, SEQ ID NO:5, SEQ ID NO:6, SEQ ID NO:9, SEQ ID NO:10 and SEQ ID NO:11.

In another aspect, the invention provides a method for the treatment or prevention of hypercholesterolemia, comprising the steps of: (a) adding oil body associated protein to a selected foodstuff; and (b) providing the foodstuff to a subject in need thereof in a quantity sufficient to treat or prevent hypercholesterolemia. The method may further comprise adding at least one compound to the foodstuff selected from the group consisting of a saponin, a phytoestrogen, a phospholipid, and a carbohydrate substantially resistant to digestion. In one embodiment, the oil body associated protein comprises lipoproteins, for example, oleosin. In another embodiment, the foodstuff is a soy-based. Examples of foodstuffs include soy flour, soy grit, soy meal, soy flakes, soy milk powder, soy protein concentrate, soy protein isolate and isolated soy polypeptide. The foodstuff may lack or comprise oil body associated body protein prior to the step of adding. The soy protein isolate may comprise a high molecular weight fraction of a soy material treated with a protease. In certain embodiments of the invention, the isolated soy polypeptide comprises β-conglycinin, or a fragment hereof, and/or is glycinin, or a fragment thereof.

In yet another aspect, the invention provides a method for the treatment or prevention of hypercholesterolemia, comprising administering a pharmaceutical composition comprising a therapeutically effective amount of purified oil body associated protein to a subject in need thereof. The pharmaceutical composition may be administered in any manner, including as a pill or capsule or as a nutritional supplement. In the method, cardiovascular disease may be prevented by decreasing the concentration of total serum and/or liver cholesterol or triglycerides. Serum cholesterol concentration may be lowered by decreasing the concentration of low density lipoprotein, increasing the concentration of high density lipoprotein and.

In still yet another aspect, a polypeptide is provided having the amino acid sequence of SEQ ID NO:1, or an amino acid sequence having at least 95% sequence homology thereto and having the same biological activity thereof.

BRIEF DESCRIPTION OF THE DRAWINGS

These and other features, aspects, and advantages of the present invention will become better understood with regard to the following description, appended claims and accompanying figures where:

FIG. 1 depicts the sequence of the oleosin protein P24 Oleosin Isoform A (P89) from soy, Accession No. P29530, and corresponds to SEQ ID NO:12.

FIG. 2 depicts the sequence of the oleosin protein P24 Oleosin Isoform B (P91) from soy, Accession No. P29531, and corresponds to SEQ ID NO:13.

FIG. 3 depicts the amino acid sequence of the oil body associated protein 17 kDa oleosin (oleo17) from maize (*Zea mays*) (Accession No. AAA68066), and corresponds to SEQ ID NO:14.

FIG. 4 depicts the amino acid sequence of the oil body associated protein 16 kDa oleosin (oleo16) from maize (*Zea mays*) (Accession No. AAA68065, and corresponds to SEQ ID NO:15.

FIG. 5 depicts the amino acid sequence of the oleosin KD18 (KD18; L2) from maize (*Zea mays*)(Accession No. AAA67699), and corresponds to SEQ ID NO:16.

FIG. 6 depicts the amino acid sequence of the *H. annuus* (sunflower) oleosin (Accession No. CAA55348), and corresponds to SEQ ID NO:17.

DETAILED DESCRIPTION OF THE INVENTION

Figure 7:
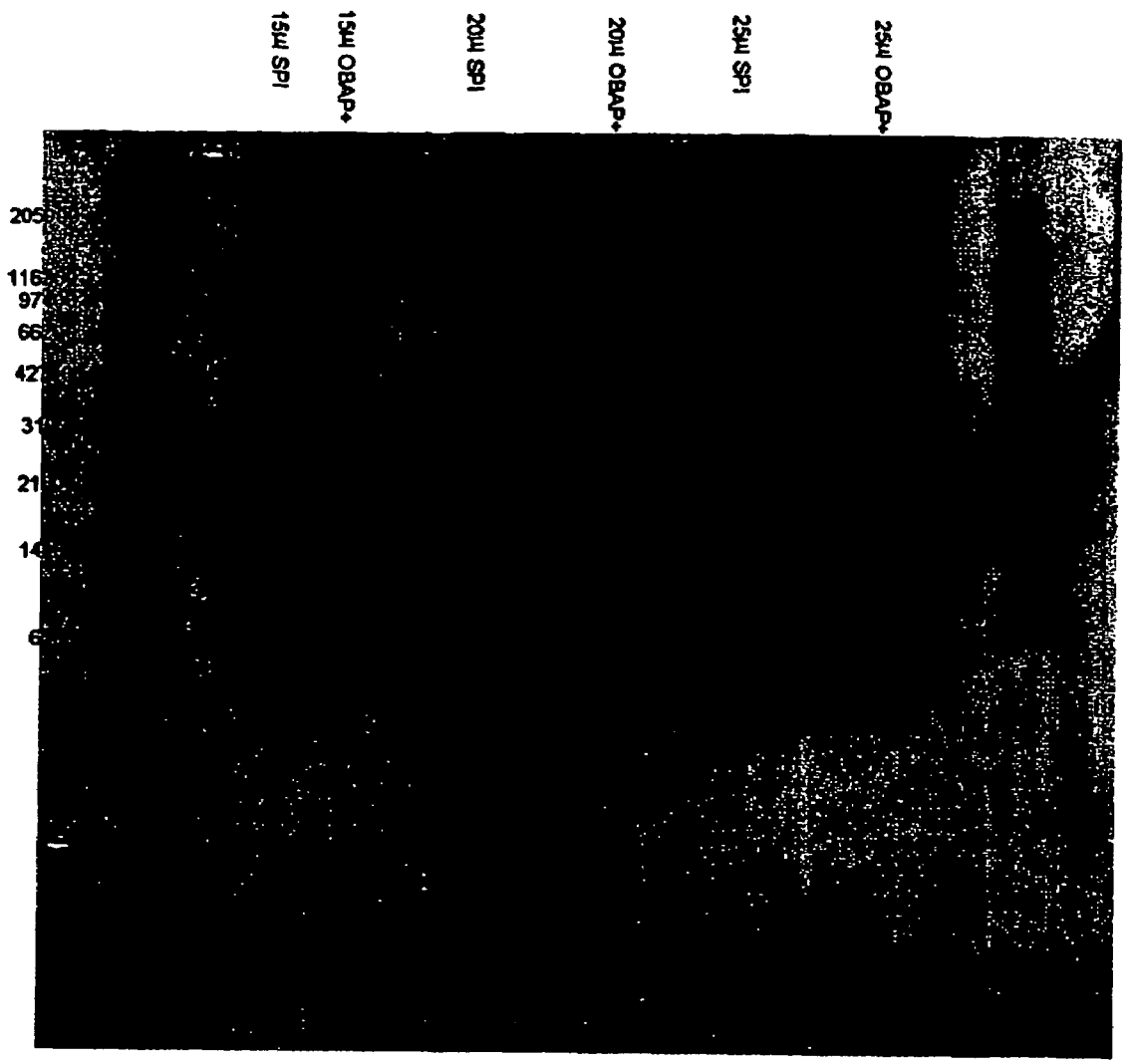
FIG. 7 depicts five polypeptide containing bands of a gel which were separated by polyacrylimide gel electrophoresis of HMF from the soy protein isolate called OBAP(+).

The invention overcomes the limitations of the prior art by identifying compositions with cardiovascular health benefits. In particular, one aspect of the invention concerns the discovery that oil body associated proteins have the ability to lower cholesterol levels. While plant components, such as soy protein, have been known to have hypocholesterolemic activity, the particular constituents responsible for this activity have not been previously characterized. The current invention, therefore, relates to the discovery of the ability of oil body associated proteins, including, oleosins and egg yolk lipoproteins, to impart upon plant proteins a characteristic ability to lower cholesterol. Equally, the present invention resides in the synergistic combination of these particular components with plant material such as soy foodstuffs. Without being bound to any particular theory, it is believed that the oil body associated proteins prevent the digestion of bioactive peptides present in soy material and thereby synergistically enhance the hypocholesterolemic activity of the composition. Additionally, the present invention relates to the synergistic combination of components in combination with soy material and an additive component selected from the group consisting of a saponin, a phytoestrogen, a phospholipid, and a carbohydrate substantially resistant to digestion, or any combination thereof, to further enhance the hypocholesterolemic activity of the combination. The present invention also encompasses the therapeutic use of these peptides, either alone or in combination with other compounds, to lower total cholesterol concentration in the blood, and in particular to decrease LDL-cholesterol concentration, to inhibit the development of cardiovascular disease.

Oil bodies are small, spherical, subcellular organelles encapsulating stored triacylglycerides, an energy reserve used by many plants. Although found in most plants and in different tissues, they are particularly abundant in the seeds of oilseeds, where they commonly range in size from under one micron to a few microns in diameter. Oil bodies are typically comprised of triacylglycerides and surrounded by lipoproteins and proteins. An "oil body associated protein" includes any and all of these proteins and lipoproteins which are physically associated with oil bodies. In plants, the major oil body associated proteins are oleosins. Oleosins have been cloned and sequenced from many plant sources including corn, rapeseed, carrot and cotton. Oleosins from different species typically are highly conserved.

I. Abbreviations and Definitions

To facilitate understanding of the invention, a number of terms and abbreviations as used herein are defined below:

HMF=high molecular weight fraction

As used herein, "high molecular weight fraction" refers to the fraction of plant protein isolate which remains after hydrolytic or chemical digestion of the isolate which can be separated by centrifugation at 4,000 to 10,000×g for 15 to 20 min at a pH 6-7.

As used herein, "additive compound" refers collectively to a single compound or a group of compounds added to the composition of the invention. These compounds are selected from the group consisting of saponin, phytoestrogen, phospholipid, and carbohydrate.

As used herein, the term "amino acid" is used in its broadest sense, and includes naturally occurring amino acids as well as non-naturally occurring amino acids, including amino acid analogs and derivatives. The latter includes molecules containing an amino acid moiety. One skilled in the art will recognize, in view of this broad definition, that reference herein to an amino acid includes, for example, naturally occurring proteogenic L-amino acids; D-amino acids; chemically modified amino acids such as amino acid analogs and derivatives; naturally occurring non-proteogenic amino acids such as norleucine, (β-alanine, ornithine, etc.; and chemically synthesized compounds having properties known in the art to be characteristic of amino acids.

As used herein, the term "proteogenic" indicates that the amino acid can be incorporated into a peptide, polypeptide, or protein in a cell through a metabolic pathway.

As used herein, the term "pharmaceutically acceptable salts" embraces salts commonly used to form alkali metal salts and addition salts of free acids or free bases. The nature of the salt is not critical, provided that it is pharmaceutically acceptable.

As used herein, "secretion sequence" or "signal peptide" or "signal sequence" means a sequence that directs newly synthesized secretory or membrane proteins to and through membranes of the endoplasmic reticulum, or from the cytoplasm to the periplasm across the inner membrane of bacteria, or from the matrix of mitochondria into the inner space, or from the stroma of chloroplasts into the thylakoid. Fusion of such a sequence to a gene that is to be expressed in a heterologous host ensures secretion of the recombinant protein from the host cell.

As used herein, "polypeptide" and "oligopeptide" are used interchangeably and mean a polymer of at least 2 amino acids joined together by peptide bonds.

As used herein, "sequence" means the linear order in which monomers occur in a polymer, for example, the order of amino acids in a polypeptide or the order of nucleotides in a polynucleotide.

As used herein, "Comminuted whole soy beans" include, for example, a soy material formed by flaking or grinding whole soybeans, including the hull and germ of the soybeans. A comminuted whole soybean material may contain fat inherent in soy or may be defatted.

As used herein, "Soy flour" includes, for example, a soy material containing less than 65% soy protein content by weight on a moisture free basis which is formed from dehulled soybeans and which has an average particle size of 150 microns or less. The term "Soy flour" may include, for example, soy milk powder. A soy flour may contain fat inherent in soy or be defatted.

As used herein, "Soy grit" includes, for example, a soy material containing less than 65% soy protein content by weight on a moisture free basis which is formed from dehulled soybeans and which has an average particle size of from 150 microns to 1000 microns. A soy grit may contain fat inherent in soy or may be defatted.

As used herein, "Soy meal" includes, for example, a soy material containing less than 65% soy protein content by weight on a moisture free basis which is formed from dehulled soybeans which does not fall within the definition of a soy flour or a soy grit. A soy meal may contain fat inherent in soy or may be defatted.

As used herein, "Soy flakes" include, for example, a soy protein material that is a flaked soy material containing less than 65% soy protein content by weight on a moisture free basis formed by flaking dehulled soybeans. Soy flakes may contain fat inherent in soy or may be defatted.

As used herein, "Soy protein concentrate" include, for example, a soy protein material prepared from high quality sound, clean, dehulled soybean seeds. Soy protein concentrate may be prepared by removing most of the oil and water soluble non-protein constituents and typically contain not less than 65% protein on a moisture free basis. In another embodiment, "Soy protein concentrate" may also be construed to additionally comprise mixtures of soy proteins and phospholipids where the total protein on a moisture free basis is between about 65 to about 90% protein. Typically, this is produced from dehulled, defatted soybeans by three basic processes: acid leaching (at about pH 4.5), extraction with alcohol (about 55-80%), and denaturing the protein with moist heat prior to extraction with water. Low water-soluble (aqueous alcohol extraction) soy protein concentrate is subjected to heat (steam injection or jet cooking) and mechanical working (homogenization) to increase solubility and functionality. When referring to mixtures of soy proteins and phospholipids where the total protein on a moisture free basis is between 65 and 90% protein, such material may be prepared by combining soy protein isolate with phospholipids or by fractionating a phospholipid:protein complex from soybeans (i.e., oil body proteins and associated phospholipids). The term "Soy protein concentrate" may include, for example, soy milk powder.

As used herein, "Soy protein extract" includes, for example, soy protein concentrate or isolate enriched in certain soy proteins. A soy protein material fractionated from the whole soy protein material may be prepared, for example, from soy protein ingredient waste or whey streams (alcohol or acidic water extraction steps).

As used herein, "Soy protein isolate" includes, for example, a soy protein material which is the major proteinaceous fraction of soybeans prepared from dehulled soybeans by removing the majority of non-protein compounds and preferably does not contain less than 90% protein on a moisture free basis. In yet another embodiment, "Soy protein isolate" may also be construed to additionally include soy protein materials enriched in certain types of soy proteins such as, for example, β-conglycinins, glycinins and oleosins, or alternatively to lack certain types of soy proteins, such as oleosins. The protein is typically extracted from unheated defatted soybean flakes with water or mild alkali in a pH range of 8-9, followed by centrifuging to remove insoluble fibrous residue; adjusting resulting extract to pH 4.5 where most of the protein precipitates as a curd; separating curd by centrifugation from the soluble oligosaccharides, followed by multiple washings, neutralized with sodium or potassium hydroxide (to make it more soluble and functional), heat-treated (e.g. using jet-cooker) and spray-dried. The addition of proteases before the heat-treatment step may also be used to partially hydrolyze the proteins and improve the solubility of soy protein isolates.

As used herein, "peptide" and "protein" are used interchangeably and mean a compound that consists of two or more amino acids that are linked by means of peptide bonds.

As used herein "recombinant protein" means that the protein, whether comprising a native or mutant primary amino acid sequence, is obtained by expression of a gene carried by a recombinant DNA molecule in a cell other than the cell in which that gene and/or protein is naturally found. In other words, the gene is heterologous to the host in which it is expressed. It should be noted that any alteration of a gene, including the addition of a polynucleotide encoding an affinity purification moiety to the gene, makes that gene unnatural for the purposes of this definition, and thus that gene cannot be "naturally" found in any cell.

As used herein, "targeting sequence" means in the context of proteins or peptides, "targeting sequence" refers to a nucleotide sequence encoding an amino acid sequence the presence of which results in a protein being directed to a particular destination within a cell.

The phrase "therapeutically-effective" indicates the capability of an agent to prevent, or improve the severity of the disease, while avoiding adverse side effects typically associated with alternative therapies. The phrase "therapeutically-effective" is to be understood to be equivalent to the phrase "effective for the treatment or prevention", and both are intended to qualify, e.g., the amount of the compositions used in the methods of the present invention which will achieve the goal of decreasing the risk of cardiovascular disease or preventing said disease while avoiding adverse side effects typically associated with alternative therapies.

II. Polypeptides of the Invention

Applicants have identified sequences of polypeptides isolated from soy material, and more specifically from the HMF of soy material, that have hypocholesterolemic activity. These sequences encode peptides from glycinin or β-conglycinin.

The proteins glycinin and β-conglycinin are seed storage proteins. Glycinin has an approximate molecular weight of 320 kilodaltons ("kDa") and is composed of six subunits, each of which consists of an acidic and a basic subunit. Moreover β-conglycinin has an approximate molecular weight of 150 kDa and is composed of three different kinds of subunits (α, α', and β) in varying proportions. Glycinin and β-conglycinin type proteins are highly conserved across different plant species.

One aspect of the present invention, therefore, encompasses one to several isolated polypeptides or polypeptide fragments from a glycinin protein. In one embodiment, the sequence of the isolated polypeptide is provided in SEQ ID NO:1 and corresponds to VFDGELQEGRVLIVPQNFVVAARSQSDNFEYVSFK.

In yet a further aspect of the present invention is provided one to several isolated polypeptides or polypeptide fragments from a β-conglycinin protein. In one embodiment, the sequence of the isolated polypeptide is provided in SEQ ID NO:2 and corresponds to LRMITLAIPVNKPGRFESFFL. In another embodiment, the sequence of the isolated polypeptide is provided in SEQ ID NO:3 and corresponds to IFVIPAGYPVVVNATSHLNFFAIGI. In yet another embodiment, the sequence of the isolated polypeptide is provided in SEQ ID NO:4 and corresponds to LQESVIVEISKK. In still another embodiment, the sequence of the isolated polypeptide is provided in SEQ ID NO:5 and corresponds to QQQEEQPLEVRK. In still yet another embodiment, the sequence of the isolated polypeptide is provided in SEQ ID NO:6 and corresponds to NQYGHVR. In still another embodiment, the sequence of the isolated polypeptide is provided in SEQ ID NO:7 and corresponds to AIVILVINEGDANIELVGL. In yet another embodiment, the sequence of the isolated polypeptide is provided in SEQ ID NO:8 and corresponds to NILEASYDTKFEEINK. In still yet another embodiment, the sequence of the isolated polypeptide is provided in SEQ ID NO:11 and corresponds to IFVIPAGYPVVVNATSDLNFFAFGI.

Applicants have also identified sequences of oleosins that demonstrate hypocholesterolemic activity. Oleosins are primarily found in membrane constituents of plant oil bodies. Oleosin proteins are comprised of three domains; the two ends of the protein, N- and C-termini, are largely hydrophillic and reside on the surface of the oil body exposed to the cytosol while the highly hydrophobic central core of the oleosin is firmly anchored within the membrane and triacylglyceride. Oleosins also contain an amphipathic alpha-helical domain at or near the C-terminus. Oleosins from different species represent a small family of proteins showing considerable amino acid sequence conservation, particularly in the central region of the protein. Within an individual species, a small number of different isoforms may exist.

Another aspect of the present invention, therefore, encompasses one to several isolated polypeptides or polypeptide fragments from an oleosin protein. In one embodiment, the oleosin is P24 isoform A (P89) from soy (Accession No. P29530; SEQ ID NO:12), which corresponds to FIG. 1. In yet another embodiment the oleosin is P24 isoform B (P91) from soy (Accession No. P29531; SEQ ID NO:13), which corresponds to FIG. 2. In still another embodiment, the oleosin is the oil body associated protein 17 kDa oleosin (oleo17) from maize (*Zea mays*) (Accession No. AAA68066; SEQ ID NO:14), which corresponds to FIG. 3. In still yet another embodiment, the oleosin is the oil body protein 16 kDa oleosin (oleo16) from maize (*Zea mays*) (Accession No. AAA68065; SEQ ID NO:15), which corresponds to FIG. 4. In yet still another embodiment, the oleosin is the oleosin KD18 (KD18; L2) from maize (*Zea mays*) (Accession No. AAA67699; SEQ ID NO 16), which corresponds to FIG. 5. In another embodiment, the oleosin is the *H. annuus* oleosin (sunflower) (Accession No. CAA55348; SEQ ID NO:17), which corresponds to FIG. 6. In still a further embodiment, the sequence of the isolated oleosin polypeptide is provided in SEQ ID NO:9 and corresponds to VKFITAATIGITLLLL. In yet another embodiment, the sequence of the isolated oleosin polypeptide is provided in SEQ ID NO:10 and corresponds to YETNSSLNNPPSR.

Also included in the present invention are polypeptides that have 90%, preferably 95%, more preferably 97%, and still more preferably 99% sequence homology with oleosin and the sequences of SEQ ID NOs: 12, 13, 14, 15, 16, 17. A further embodiment of the invention provides polypeptides that have 90%, preferably 95%, more preferably 97%, and still more preferably 99% sequence homology with any of the sequences of SEQ ID NO:1-11.

"Homology", as is well understood in the art, is a relationship between two or more polypeptide sequences or two or more polynucleotide sequences, as determined by comparing the sequences. In the art, "homology" also means the degree of sequence relatedness between polypeptide or polynucleotide sequences, as determined by the match between strings of such sequences. "Homology" can be readily calculated by known methods including, but not limited to, those described in *Computational Molecular Biology*, 1988; *Biocomputing: Informatics and Genome Projects*, 1993; *Computer Analysis of Sequence Data, Part I*, 1994; *Sequence Analysis in Molecular Biology*, 1987; *Sequence Analysis Primer*, 1991; and Carillo and Lipman, 1988. Methods to determine homology are designed to give the largest match between the sequences tested. Moreover, methods to determine homology are codified in publicly available programs. Computer programs which can be used to determine identity/homology between two sequences include, but are not limited to, GCG (Devereux et al., 1984); suite of five BLAST programs, three designed for nucleotide sequences queries (BLASTN, BLASTX, and TBLASTX) and two designed for protein sequence queries (BLASTP and TBLASTN) (Coulson, 1994; Birren, et al., 1997). The BLAST X program is publicly available from NCBI and other sources (*BLAST Manual*, Altschul et al., 1990). The well known Smith Waterman algorithm can also be used to determine homology.

The present invention also relates to the isolated proteins. As used herein the term protein includes fragments, analogs and derivatives of the glycinin, β-conglycinin, or oleosin protein. The protein of the present invention can be a natural protein, a recombinant protein or a synthetic protein or a polypeptide.

Those of ordinary skill in the art are aware that modifications in the amino acid sequence of a peptide, polypeptide, or protein can result in equivalent, or possibly improved, second generation peptides, etc., that display equivalent or superior functional characteristics when compared to the original amino acid sequence. The present invention accordingly encompasses such modified amino acid sequences. Alterations can include amino acid insertions, deletions, substitutions, truncations, fusions, shuffling of subunit sequences, and the like, provided that the peptide sequences produced by such modifications have substantially the same functional properties as the naturally occurring counterpart sequences disclosed herein. Biological activity or function can be determined by, for example, the ability of the protein to lower total serum cholesterol as depicted in the examples below.

One factor that can be considered in making such changes is the hydropathic index of amino acids. The importance of the hydropathic amino acid index in conferring interactive biological function on a protein has been discussed by Kyte and Doolittle (1982). It is accepted that the relative hydropathic character of amino acids contributes to the secondary structure of the resultant protein. This, in turn, affects the interaction of the protein with molecules such as enzymes, substrates, receptors, DNA, antibodies, antigens, etc.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide or protein can be substituted for other amino acids having a similar hydropathic index or score and produce a resultant peptide or protein having similar biological activity, i.e., which still retains biological functionality. In making such changes, it is preferable that amino acids having hydropathic indices within ±2 are substituted for one another. More preferred substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4). Thus, one amino acid in a peptide, polypeptide, or protein can be substituted by another amino acid having a similar hydrophilicity score and still produce a resultant protein having similar biological activity, i.e., still retaining correct biological function. In making such changes, amino acids having hydropathic indices within ±2 are preferably substituted for one another, those within ±1 are more preferred, and those within ±0.5 are most preferred.

As outlined above, amino acid substitutions in the peptides of the present invention can be based on the relative similarity of the amino acid side-chain substituents, for example, their hydrophobicity, hydrophilicity, charge, size, etc. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine. It should be noted that changes which are not expected to be advantageous can also be useful if these result in the production of functional sequences.

The term protein also includes forms of the protein to which one or more substituent groups have been added. A substituent is an atom or group of atoms that is introduced into a molecule by replacement of another atom or group of atoms. Such groups include, but are not limited to lipids, phosphate groups, sugars and carbohydrates. Thus, the term protein includes, for example, lipoproteins, glycoproteins, phosphoproteins and phospholipoproteins.

III. Compositions and Methods of the Invention

Another aspect of the invention provides compositions that are useful for treatment or prevention of cardiovascular disease. The composition in one embodiment encompasses a plant-based foodstuff to which isolated oil body associated protein has been added. In one embodiment of the invention, the foodstuff is soy-based. In yet another embodiment, the composition comprises an isolated soy material, an isolated oil body associated protein, and at least one additive compound selected from the group consisting of a saponin, phytoestrogen, a phospholipid, and a carbohydrate substantially resistant to digestion. In certain embodiments of the invention, an isolated oil body associated protein may be a purified fraction isolated away from plant protein. For example, isolated oil body associated protein may be enriched 1, 10, 100, 200, 1000 or more fold relative to crude plant proteins. In certain embodiments of the invention, the isolated oil body associated protein may be enriched for oil body associated protein 1, 5, 10, 50 or 100 or more fold relative to, for example, a purified fraction such as HMF.

An isolated soy material employed in the present invention may be prepared and isolated from any soy plant, to the extent the isolate soy material contains the constituents necessary for the isolated soy material to exhibit the desired hypocholesterolemic activity. Isolated soy material may comprise, for example, comminuted whole soy beans, soy flour, soy milk powder, soy grit, soy meal, soy flakes, soy concentrate, soy protein isolate, and soy protein extract. In one embodiment, the soy material is soy concentrate. In yet another embodiment, the soy material is soy protein isolate. In still a further embodiment, the soy material is soy protein extract. Any method known in the art, including those methods detailed herein, may be employed to isolate the particular soy material.

One aspect of the present invention provides isolated soy material enriched with certain soy proteins or peptides, such as β-conglycinins, glycinins and oleosins. These soy materials can be prepared from isolates, concentrates, or from the waste streams of isolate and concentrate manufacture. They can also be prepared from soybeans with a modified protein composition, such as soybeans having twice the normal levels of β-conglycinin and low levels of glycinin (as described in, for example, U.S. Pat. No. 6,171,640).

Preparation of foodstuffs is well known to those of skill in the art. In the case of soy, common food usage includes, but is not limited to, products such as the seed, bean sprouts, baked soybean, full fat soy flour used in various products of baking, roasted soybean used as confectioneries, soy nut butter, soy coffee, and other soy derivatives of oriental foods. Soy protein products (e.g., meal), can be divided into soy flour concentrates and isolates which have both food/feed and industrial use. Soy flour and grits are often used in the manufacturing of meat extenders and analogs, pet foods, baking ingredients and other food products. Food products made from soy flour and isolate include baby food, candy products, cereals, food drinks, noodles, yeast, beer, ale, etc.

In certain aspects of the present invention, isolated soy material which lack, or contain low amounts of, certain types of soy proteins, such as, for example, oleosins, are fortified with oil body associated proteins, such as, for example, oleosins, thereby improving or restoring the hypocholesterolemic properties of the soy protein or soy protein composition. In further embodiments of the invention, oil body associated proteins are added to a final concentration of about 0.5%, 1%, 3%, 5%, 10%, 20% or more by weight, including all intermediate ranges within these concentrations. Depending on the particular application, soy materials without oleosin, or with decreased amounts of oleosin, may be highly beneficial. For example, oleosins may be considered undesirable because they bind flavors contributing to the relatively poor flavor quality of soy foods. Moreover, oleosins are also poorly soluble and contribute to the large particle fraction when defatted soymilk is dispersed in water. In one embodiment, the oleosin may be removed by allowing the large particle fraction containing oleosin to settle in a tank or by using ultrafiltration membranes. Alternatively, the oleosins can be precipitated from soy protein isolate at pH 2.8 in the presence of sodium sulfate and calcium chloride (Samoto et al., 1998).

Also encompassed within the present invention is a composition comprising an isolated soy material and an isolated oil body associated protein wherein the isolated soy material is a high molecular weight fraction ("HMF") of a soy protein isolate. The HMF employed in any of the compositions of the invention may be prepared and isolated from any plant protein isolate in which it naturally occurs to the extent the fraction possesses the desired hypocholesterolemic activity. In one embodiment, the HMF is prepared from a soy protein source. Typical soy material from which the HMF may be prepared include soy beans, dehulled soy beans, soy meal, soy flour, soy grits, soy milk powder, soy flakes (full fat and defatted), soy molasses, soy protein concentrate, soy whey, soy whey protein, and soy protein isolate. In a preferred embodiment, the HMF is prepared from a soy protein isolate.

In order to prepare the HMEF, the selected plant protein isolate is subjected to hydrolytic or chemical digestion. Typical agents employed for this digestion process include pepsin or microbial proteases. Typically, for example, the soy protein is incubated with the pepsin enzyme for 13 to 17 hrs, (0.2% NaCl in aqueous phase, 38° C., pH 1.1) with the pepsin enzyme being 0.5 to 5% of soy protein isolate), heat-treated for 20 min at 90° C. to inactivate the pepsin, cooled on ice, adjusted to a pH of 6 to 7 with $Na_2CO_3$, and centrifuged at 4,500 g for 20 min. This pellet can then be washed 3 times with water and identified. Other methods of use of pepsin enzyme are well known in the art.

Microbial proteases, for example, can be Sumizyme FP (*Aspergillus niger* protease, enzyme activity 48800 U/gm, Shin Nippon Kagaku Kabushiki Kaisha) and incubated with the soy protein at 60° C. for five hrs. When using such a solution, rather than adjusting pH, the solution is diluted with water. Centrifugation at 10,000×g can then be carried out for 10 min. The precipitate can then be collected and identified. Additional methods are known in the art. See, for example, Hori et al. (1999).

The HMF is then isolated from the digested plant protein isolate by any mean generally known in the art. In one embodiment, the HMF is isolated by centrification. Typically, the isolation process may be performed, for example, by drying (e.g., freeze drying) the fraction after centrifugation of an aqueous suspension of soy protein isolate which was treated with a microbial protease or pepsin (protease is 0.5-6% of total protein) and incubating at 30-70° C. for 1-20 hrs. Additional methods are well known in the art. See, Nagoako et al., (1999).

Moreover, any peptide isolated from the HMF may be employed in the composition of the invention to the extent that the peptide possesses the desired hypocholesterolemic activity. Typically, however, the peptide utilized in the composition is at least 10 amino acid residues in length, more typically is from about 10 to about 100 amino acid residues in length, and most typically is about 30 to about 80 amino acid residues in length. Also, generally speaking, the peptide is substantially hydrophobic in nature having from about over 30 weight percent to preferably about over 35 weight percent of hydrophobic amino acid composition. In addition, the peptide employed may have 0, 1, or more amphipathic regions. Additionally, the peptide employed may have a hydrophobic surface or hydrophobic region that is a result not of a string of hydrophobic amino acids, but of the α-helical structure of the peptide.

Another embodiment of the present invention provides a composition comprising isolated soy polypeptides isolated from the soy material wherein the soy polypeptides comprise β-conglycinin and glycinin. The structure of both β-conglycinin and glycinin was detailed above and a detailed review of their structures is provided in Utsumi et al. (1997). Without limiting Applicants to a single theory, it is believed that these peptides impart their hypocholesterolemic activity because they are able to survive digestion and become absorbed into the blood stream or bind to bile acids. Also beneficial, though not required, is the presence of an amphipathic α-helical region within the β-conglycinin. Without limiting the Applicants to any single theory, it is believed that the presence of an amphipathic α-helical region is beneficial because it forms a hydrophobic surface that facilitates interaction with various receptor sites important for imparting hypocholesterolemic activity.

Additionally, and without limiting Applicants to any single theory, the identified polypeptides of the invention may also serve as a source of nitrogen to beneficial bacteria in the colon. These bacteria can then produce short chain fatty acids such as propionate acid which positively affect lipid metabolism. The short chain fatty acids inhibit synthesis of fatty acids in the liver, lowering the rates of triglyceride secretion and also reduce hepatic cholesterol synthesis. An aspect of the invention is the use of soy protein polypeptides to promote the production of short chain fatty acids in the colon and reduce serum cholesterol and triglycerides. The effectiveness of undigested soy polypeptides in promoting the growth of beneficial colonic bacteria will be most significant in the presence of undigested carbohydrates such as high amylose cornstarch which are an important fuel for human colonic microflora. Therefore another embodiment of the invention is the combination of soy polypeptide ingredients with sources of undigested carbohydrates to optimize the beneficial effects of polypeptides on serum cholesterol and triglycerides.

One aspect of the invention, therefore, provides compositions having specific polypeptides isolated from β-conglycinin. Generally speaking, these polypeptide sequences correspond to any one of the amino acid sequences of SEQ ID NO:2, SEQ ID NO:3, SEQ ID NO:4, SEQ ID NO:5, SEQ ID NO:6, and SEQ ID NO:11. These sequences may be isolated from β-conglycinin by a method, for example, involving (1) enzymatic hydrolysis of soy material followed by isolation of the high molecular weight fraction, e.g. by centrifugation or (2) enzymolysis of soy material followed by further purification by an ultrafiltration membrane, ion exchange resin column, and gel filtration column chromatography giving peptides of a molecular weight range of approximately 200 to about 5,000 kilodaltons (see, for example, the method detailed in Yamauchi and Suetsuna (1993). The peptides can be fractionated further by using ion-exchange chromatography (Chen et al., 1995). Alternatively, rather than isolate the individual sequences from the particular β-conglycinin subunits, it is also possible to utilize soybeans having twice the normal levels of β-conglycinin and merely isolate the β-conglycinin from the soybeans. Likewise, it is also possible to utilize the same germplasm where only a particular β-conglycinin subunit is expressed in order to obtain crude preparations of this subunit. The active peptides are then produced after consumption of the crude preparations as a result of hydrolyzation in the gut by pepsin and pancreatin, or are obtained during ingredient manufacture using microbial enzymes. Therefore, in another embodiment of the invention is provided a composition comprising a crude preparation of a particular subunit of β-conglycinin combined with an oleosin preparation.

Yet another aspect of the invention provides compositions having specific polypeptides isolated from glycinin. In one embodiment the composition contains a polypeptide isolated from the basic subunit of glycinin. In yet another embodiment, the composition comprises a polypeptide isolated from the B-1b subunit of glycinin. In a preferred embodiment, the composition comprises a peptide isolated from glycinin which corresponds to the anino acid sequence of SEQ ID NO:1. Typically glycinin is isolated from protein sources using isolation procedures that are well known in the art. An example of these isolation procedures are those used to isolate other protein isolates, as outlined above.

The compositions of the invention typically also contain an oil body associated protein. As used herein, the term "oil body associated protein" includes any protein, lipoprotein or peptide physically associated with an oil body structure or intracellular lipid particle. Generally speaking, most eukaryotic cells from species such as plants, mammals, non-mammalian cells, algae and yeast contain intracellular lipid particles. These particles are known as lipid bodies, lipid droplets or, especially in plants, oil bodies, oleosomes, or spherosomes, depending upon the species. The lipid particles of eukaryotic cells consist of a highly hydrophobic core of neutral lipids, mainly triacylglycerols and/or steryl esters, surrounded by a phospholipid monolayer with a small amount of proteins embedded. A typical composition of oil bodies isolated from maize is triacylglycerols (95%), diacylglycerols (4%), phospholipids (0.9%) and protein (1.4%).

Typical oil body associated proteins useful in the compositions of the invention include oil body proteins such as oleosins in the form of apoproteins or as lipoproteins and a 34-kD soybean seed storage vacuole protein that associates with the oil bodies. One aspect of the invention, therefore, provides a composition that comprises an isolated soy material and a peptide isolated from an oil body associated protein wherein the peptide is an oleosin or a peptide fragment from an oleosin. The oleosin may be represented by the sequences of P24 Oleosin Isoform A (P89) Accession No. P29530, as is provided in SEQ ID NO:12 and corresponding to FIG. 1, P24 Oleosin Isoform B (P91) Accession No. P29531, as is provided in SEQ ID NO:13 and corresponding to FIG. 2, the oil body associated protein 17 kDa oleosin (oleo17) Accession No. AAA68066, as provided in SEQ ID NO:14 and corresponding to FIG. 3, the oil body protein 16 kDa oleosin (oleo16) Accession No. AAA68065, as provided in SEQ ID NO:15 and corresponding to FIG. 4, the oleosin KD18 (KD18; L2) Accession No. AAA67699, as provided in SEQ ID NO 16 and corresponding to FIG. 5, and the *H. annuus* oleosin Accession No. CAA55348, as provided in SEQ ID NO:17 and corresponding to FIG. 6. More typically, the peptide employed in the composition is from a low molecular weight oleosin with an approximate molecular weight of 17 kilodaltons. In certain embodiments, the peptide is from an oleosin and will correspond to the amino acid sequence of SEQ ID NO:9 or SEQ ID NO:10.

The oleosin peptide employed in the composition of the invention may be isolated from intact oil bodies. Toward that end, intact oil bodies may be isolated from seeds as a source of oil body associated proteins. Methods and lists of seed types that can be used are provided, for example, in WO 00/30602. Methods for preparing oil bodies are also described in Japanese Patent App. Pub. No. 2002-101820. The oil may be extracted from the oil bodies with diethyl ether, leaving the interfacial materials (oleosins and phospholipids) in the aqueous fraction. The phopholipids may be extracted using choroform/methanol (2:1, vol/vol) or other suitable organic solvents. In particular, oleosins are isolated as the aggregated fraction (Tzen and Huang 1992). In addition, a high pH extraction may be used to remove P34 protein, if present. The P34 protein has an isoelectric pH below 6.5, and therefore, will be soluble at high pH where oleosins have their isoelectric pH and precipitate.

Oleosins may also be isolated from whole soybeans soaked in water or from defatted soy flour. Oleosin may be isolated from protein sources using isolation procedures that are well known in the art. An example of these isolation procedures are those used to isolate oleosins from defatted soy flour, as outlined above. Another example is the isolation of oleosins from whole soybeans (JP 2002-101820). Additional sources of oleosins include plant cells, fungal cells, yeast cells, (Leber et al., 1994), bacterial cells, (Pieper-Fürst et al., 1994) and algae cells (Roessler, 1988). In preferred embodiments of the invention, oleosins are obtained from a plant cell which includes cells from pollens, spores, seed, and vegetative plant organs in which oleosins or oil-body like organelles are present (Huang, 1992). More preferably, the oleosins of the present invention are obtained from a plant seed and most preferably from the group of plant species comprising: rapeseed (*Brassica* spp), soybean (*Glycine max*), sunflower (*Helianthus annuus*), oil palm (*Elaeis guineeis*), cottonseed (*Gossypium* spp.), groundnut (*Arachis hypogaea*), coconut (*Cocus nucifera*), castor (*Ricinus cummunis*), safflower (*Carthamus tinctorius*), mustard (*Brassica* spp. and *sinapis alba*), coriander (*Coriandrum sativum*), squach (*Cucurbita maxima*), lineseed/flax (*Linum usitatissumum*), Brazil nut (*Bertholletia excelsa*), jojoba (*Simmondsia chinensis*), maize (*Zea mays*), crambe (*Crambe abyssinica*), and eruca (*Eruca sativa*).

Yet another aspect of the invention encompasses a composition that comprises an isolated soy material and a peptide isolated from an oil body associated protein wherein the peptide is a lipoprotein. Lipoproteins are noncovalent, nonstoichiometric, particulate complexes of neutral lipid, phospholipid, and protein found in both animal an plant cells. In one embodiment, the lipoprotein is a mammalian lipoprotein. In yet another embodiment, the lipoprotein is egg yolk lipoprotein (for a review of egg yolk structure, see for example, Bringe (1997), the content of which is hereby incorporated herein by reference.) In still another embodiment, the lipoprotein comprises a fat globulin membrane protein.

Lipoproteins may be isolated from oil body associated protein sources using procedures that are well known in the art. An example of these isolation procedures are those used to isolate oil body proteins or oleosins from defatted soy flour, as outlined above. Moreover, egg yolk lipoproteins may be isolated from oil body associated protein sources using isolation procedures that are well known in the art.

As an example of these isolation procedures, egg yolk lipoproteins can be isolated by extracting the triglycerides and cholesterol using supercritical carbon dioxide (see for example, Bringe and Cheng, 1995). A further aspect of the invention provides a composition comprising a soy material in combination with an oil body associated protein and an additive compound. The additive compound may include any compound that therapeutically enhances the composition. Typically, however, the additive compound is selected from the group consisting of a saponin, a phytoestrogen, a phospholipid, and a carbohydrate substantially resistant to digestion. Generally speaking, without being bound by any particular theory, it is believed that these additive compounds enhance the hypocholesterolemic activity of the composition by substantially preventing the digestion of cholesterol-lowering polypeptides in the isolated soy material. Because of these properties, the additive compounds of the invention increase the therapeutic capacity of the composition. In a preferred embodiment, accordingly, the compositions of the invention may have any combination of the specific additive components identified above in combination with an isolated soy material and an isolated oil body associated protein.

In one embodiment, therefore, a composition of the present invention may include one to several saponins as an additive compound. The saponin may be isolated from a plant source in which it naturally occurs by any known method, such as the method of Gurfinkel et al., (2002), or it can be synthetically prepared by any known method. Any saponin is suitable for use in the current invention to the extent that the compound selected enhances the properties of the composition for use as a hypocholesterolemic agent. Typically, however, the saponin employed is isolated from a legume, such as alfalfa or soybean plants, or from oats or other plant seeds. More typically, the saponin is isolated from soybean seeds, and more specifically may be isolated from the soybean germ. Sources of saponins include, for example, soybeans, quillaja, alfalfa, and soapwart. Soy saponins include, for example, saponin A, B, E, and sapogenol A, B, and E.

Moreover a composition of the invention may include one to several phytoestrogens as an additive compound. The phytoestrogen may be isolated from a plant source in which it naturally occurs by any known method, such as the method detailed in U.S. Pat. No. 5,855,892 or WO 00/30663, or it can be synthetically prepared by any known method. Any phytoestrogen is suitable for use in the current invention to the extent that the compound selected enhances the properties of the composition for use as a hypocholesterolemic agent. Typically, the phytoestrogen employed in the composition is an isoflavone. More typically, the isoflavone is genistein, daidzein (including its metabolites o-desmethylangolensin, dihydroclaidzein, and equol), biochanin A, formononetin, and their respective naturally occurring glucosides and glucoside conjugates present in soybeans or clover.

A composition of the invention may also include one to several phospholipids as an additive compound. Phospholipids may be from various sources, but are typically isolated, for example, from seeds, and more typically from the oil seeds of soy plants. These include lecithin and lyso-lecithin. Additionally, phospholipids with a modified fatty acid composition can be used. Such phospholipids can be enzyme modified soy phospholipids. Enzyme modified phospholipids may be prepared, for example, from soy phospholipids (SLP; True Lecithin, Mie, Japan) by treatment with phospholipase $A_2$ (Novo Industry, Bagsvaerd, Denmark) (Nagaoka, et al., 1999). Additionally, phospholipids with a modified fatty acid composition can be obtained from plants or plant seeds that have been genetically modified to produce phospholipids with modified fatty acid compositions. An example of a phospholipid with a modified fatty acid composition is lecithin with a modified fatty acid composition. Other methods that are well known in the art may also be used to modify the fatty acid compositions of phospholipids.

Additionally, a composition of the invention may also include one to several carbohydrates. Any carbohydrate may be utilized in a composition of the invention to the extent that the compound selected enhances the properties of the composition for use as a hypocholesterolemic agent. Typically, however, the carbohydrates employed are carbohydrates that are substantially resistant to digestion. As utilized herein, "substantially resistant to digestion" when used to describe a carbohydrate is defined, in the art, to typically mean, for example, carbohydrates that are greater than about 70% resistant to digestion, preferably greater than about 80% resistant to digestion, and more preferably greater than about 90% resistant to digestion. Generally speaking, carbohydrates rich in amylose starch or fiber are particularly suitable for use in a composition. In one embodiment, for example, the carbohydrate employed in the composition is high amylose starch, oligofructose, or soy cotyledon fiber. In addition, embodiments are, for example, starches that are physically inaccessible (partly milled grains and seeds), resistant granules (raw potato, green banana, some legumes, and high amylose starches), retrograded starches (cooked and cooled potato, bread, and cornflakes), and chemically modified starches (etherized, esterified, or cross-bonded starches (used in processed foods)) (Topping and Clifton, 2001).

Any combination of an isolated soy material and an isolated oil body associated protein, in the presence or absence of at least one additive compound, may be combined to form a composition of the invention. Table 1 below, for example, illustrates a number of typical formulations for different embodiments of compositions of the present invention.

TABLE 1

Formulations of the Composition

| Isolated Soy Material | Isolated Oil Body Associated Protein | Additive Compound |
|---|---|---|
| Soy Flour | Oleosin | No additive compound |
| Soy Flour | Oleosin | At least one additive compound |
| Soy Flour | 90%, 95%, 97% or 99% Sequence Identity to Oleosin | No additive compound |
| Soy Flour | 90%, 95%, 97% or 99% Sequence Identity to Oleosin | At least one additive compound |
| Soy Flour | Low Molecular Weight Fraction of Oleosin | No additive compound |
| Soy Flour | Low Molecular Weight Fraction of Oleosin | At least one additive compound |
| Soy Flour | 17 kDa Fraction | No additive compound |
| Soy Flour | 17 kDa Fraction | At least one additive compound |
| Soy Flour | SEQ ID NOs: 12 or 14 | No additive compound |
| Soy Flour | SEQ ID NOs: 12 or 14 | At least one additive compound |
| Soy Flour | Lipoprotein | No additive compound |
| Soy Flour | Lipoprotein | At least one additive compound |
| Soy Flour | Mammalian Lipoprotein | No additive compound |
| Soy Flour | Mammalian Lipoprotein | At least on additive compound |
| Soy Flour | Egg Yolk Lipoprotein | No additive compound |
| Soy Flour | Egg Yolk Lipoprotein | At least one additive compound |
| Soy Flour | Fat Globule Membrane Protein | No additive compound |
| Soy Flour | Fat Globule Membrane Protein | At least one additive compound |
| Soy Milk Powder | Oleosin | No additive compound |
| Soy Milk Powder | Oleosin | At least one additive compound |
| Soy Milk Powder | 90%, 95%, 97% or 99% Sequence Identity to Oleosin | No additive compound |
| Soy Milk Powder | 90%, 95%, 97% or 99% Sequence Identity to Oleosin | At least one additive compound |
| Soy Milk Powder | Low Molecular Weight Fraction of Oleosin | No additive compound |
| Soy Milk Powder | Low Molecular Weight Fraction of Oleosin | At least one additive compound |
| Soy Milk Powder | 17 kDa Fraction | No additive compound |
| Soy Milk Powder | 17 kDa Fraction | At least one additive compound |
| Soy Milk Powder | SEQ ID NOs: 12 or 14 | No additive compound |
| Soy Milk Powder | SEQ ID NOs: 12 or 14 | At least one additive compound |
| Soy Milk Powder | Lipoprotein | No additive compound |
| Soy Milk Powder | Lipoprotein | At least one additive compound |
| Soy Milk Powder | Mammalian Lipoprotein | No additive compound |
| Soy Milk Powder | Mammalian Lipoprotein | At least one additive compound |
| Soy Milk Powder | Egg Yolk Lipoprotein | No additive compound |
| Soy Milk Powder | Egg Yolk Lipoprotein | At least one additive compound |
| Soy Milk Powder | Fat Globule Membrane Protein | No additive compound |
| Soy Milk Powder | Fat Globule Membrane Protein | At least one additive compound |
| Soy Protein Concentrate | Oleosin | No additive compound |
| Soy Protein Concentrate | Oleosin | At least one additive compound |
| Soy Protein Concentrate | 90%, 95%, 97% or 99% Sequence Identity to Oleosin | No additive compound |
| Soy Protein Concentrate | 90%, 95%, 97% or 99% Sequence Identity to Oleosin | At least one additive compound |
| Soy Protein Concentrate | Low Molecular Weight Fraction of Oleosin | No additive compound |
| Soy Protein Concentrate | Low Molecular Weight Fraction of Oleosin | At least one additive compound |
| Soy Protein Concentrate | 17 kDa Fraction | No additive compound |
| Soy Protein Concentrate | 17 kDa Fraction | At least one additive compound |
| Soy Protein Concentrate | SEQ ID NOs: 12 or 14 | No additive compound |
| Soy Protein Concentrate | SEQ ID NOs: 12 or 14 | At least one additive compound |
| Soy Protein Concentrate | Lipoprotein | No additive compound |

TABLE 1-continued

Formulations of the Composition

| Isolated Soy Material | Isolated Oil Body Associated Protein | Additive Compound |
|---|---|---|
| Soy Protein Concentrate | Lipoprotein | At least one additive compound |
| Soy Protein Concentrate | Mammalian Lipoprotein | No additive compound |
| Soy Protein Concentrate | Mammalian Lipoprotein | At least one additive compound |
| Soy Protein Concentrate | Egg Yolk Lipoprotein | No additive compound |
| Soy Protein Concentrate | Egg Yolk Lipoprotein | At least one additive compound |
| Soy Protein Concentrate | Fat Globule Membrane Protein | No additive compound |
| Soy Protein Concentrate | Fat Globule Membrane Protein | At least one additive compound |
| Soy Protein Isolate | Oleosin | No additive compound |
| Soy Protein Isolate | Oleosin | At least one additive compound |
| Soy Protein Isolate | 90%, 95%, 97% or 99% Sequence Identity to Oleosin | No additive compound |
| Soy Protein Isolate | 90%, 95%, 97% or 99% Sequence Identity to Oleosin | At least one additive compound |
| Soy Protein Isolate | Low Molecular Weight Fraction of Oleosin | No additive compound |
| Soy Protein Isolate | Low Molecular Weight Fraction of Oleosin | At least one additive compound |
| Soy Protein Isolate | 17 kDa Fraction | No additive compound |
| Soy Protein Isolate | 17 kDa Fraction | At least one additive compound |
| Soy Protein Isolate | SEQ ID NOs: 12 or 14 | No additive compound |
| Soy Protein Isolate | SEQ ID NOs: 12 or 14 | At least one additive compound |
| Soy Protein Isolate | Lipoprotein | No additive compound |
| Soy Protein Isolate | Lipoprotein | At least one additive compound |
| Soy Protein Isolate | Mammalian Lipoprotein | No additive compound |
| Soy Protein Isolate | Mammalian Lipoprotein | At least one additive compound |
| Soy Protein Isolate | Egg Yolk Lipoprotein | No additive compound |
| Soy Protein Isolate | Egg Yolk Lipoprotein | At least one additive compound |
| Soy Protein Isolate | Fat Globule Membrane Protein | No additive compound |
| Soy Protein Isolate | Fat Globule Membrane Protein | At least one additive compound |
| High Molecular Weight Fraction | Oleosin | No additive compound |
| High Molecular Weight Fraction | Oleosin | At least one additive compound |
| High Molecular Weight Fraction | 90%, 95%, 97% or 99% Sequence Identity to Oleosin | No additive compound |
| High Molecular Weight Fraction | 90%, 95%, 97% or 99% Sequence Identity to Oleosin | At least one additive compound |
| High Molecular Weight Fraction | Low Molecular Weight Fraction of Oleosin | No additive compound |
| High Molecular Weight Fraction | Low Molecular Weight Fraction of Oleosin | At least one additive compound |
| High Molecular Weight Fraction | 17 kDa Fraction | No additive compound |
| High Molecular Weight Fraction | 17 kDa Fraction | At least one additive compound |
| High Molecular Weight Fraction | SEQ ID NOs: 12 or 14 | No additive compound |
| High Molecular Weight Fraction | SEQ ID NOs: 12 or 14 | At least one additive compound |
| High Molecular Weight Fraction | Lipoprotein | No additive compound |
| High Molecular Weight Fraction | Lipoprotein | At least one additive compound |
| High Molecular Weight Fraction | Mammalian Lipoprotein | No additive compound |
| High Molecular Weight Fraction | Mammalian Lipoprotein | At least one additive compound |
| High Molecular Weight Fraction | Egg Yolk Lipoprotein | No additive compound |
| High Molecular Weight Fraction | Egg Yolk Lipoprotein | At least one additive compound |
| High Molecular Weight Fraction | Fat Globule Membrane Protein | No additive compound |
| High Molecular Weight Fraction | Fat Globule Membrane Protein | At least one additive compound |
| Isolated Soy Polypeptide | Oleosin | No additive compound |
| Isolated Soy Polypeptide | Oleosin | At least one additive compound |
| Isolated Soy Polypeptide | 90%, 95%, 97% or 99% Sequence Identity to Oleosin | No additive compound |
| Isolated Soy Polypeptide | 90%, 95%, 97% or 99% Sequence Identity to Oleosin | At least one additive compound |
| Isolated Soy Polypeptide | Low Molecular Weight Fraction of Oleosin | No additive compound |
| Isolated Soy Polypeptide | Low Molecular Weight Fraction of Oleosin | At least one additive compound |
| Isolated Soy Polypeptide | 17 kDa Fraction | No additive compound |
| Isolated Soy Polypeptide | 17 kDa Fraction | At least one additive compound |
| Isolated Soy Polypeptide | SEQ ID NOs: 12 or 14 | No additive compound |
| Isolated Soy Polypeptide | SEQ ID NOs: 12 or 14 | At least one additive compound |
| Isolated Soy Polypeptide | Lipoprotein | No additive compound |
| Isolated Soy Polypeptide | Lipoprotein | At least one additive compound |
| Isolated Soy Polypeptide | Mammalian Lipoprotein | No additive compound |
| Isolated Soy Polypeptide | Mammalian Lipoprotein | At least on additive compound |
| Isolated Soy Polypeptide | Egg Yolk Lipoprotein | No additive compound |
| Isolated Soy Polypeptide | Egg Yolk Lipoprotein | At least one additive compound |
| Isolated Soy Polypeptide | Fat Globule Membrane Protein | No additive compound |
| Isolated Soy Polypeptide | Fat Globule Membrane Protein | At least one additive compound |
| Glycinin or a subunit thereof | Oleosin | No additive compound |
| Glycinin or a subunit thereof | Oleosin | At least one additive compound |
| Glycinin or a subunit thereof | 90%, 95%, 97% or 99% Sequence Identity to Oleosin | No additive compound |
| Glycinin or a subunit thereof | 90%, 95%, 97% or 99% Sequence Identity to Oleosin | At least one additive compound |
| Glycinin or a subunit thereof | Low Molecular Weight Fraction of Oleosin | No additive compound |
| Glycinin or a subunit thereof | Low Molecular Weight Fraction of Oleosin | At least one additive compound |
| Glycinin or a subunit thereof | 17 kDa Fraction | No additive compound |
| Glycinin or a subunit thereof | 17 kDa Fraction | At least one additive compound |
| Glycinin or a subunit thereof | SEQ ID NOs: 12 or 14 | No additive compound |

TABLE 1-continued

Formulations of the Composition

| Isolated Soy Material | Isolated Oil Body Associated Protein | Additive Compound |
|---|---|---|
| Glycinin or a subunit thereof | SEQ ID NOs: 12 or 14 | At least one additive compound |
| Glycinin or a subunit thereof | Lipoprotein | No additive compound |
| Glycinin or a subunit thereof | Lipoprotein | At least one additive compound |
| Glycinin or a subunit thereof | Mammalian Lipoprotein | No additive compound |
| Glycinin or a subunit thereof | Mammalian Lipoprotein | At least one additive compound |
| Glycinin or a subunit thereof | Egg Yolk Lipoprotein | No additive compound |
| Glycinin or a subunit thereof | Egg Yolk Lipoprotein | At least one additive compound |
| Glycinin or a subunit thereof | Fat Globule Membrane Protein | No additive compound |
| Glycinin or a subunit thereof | Fat Globule Membrane Protein | At least one additive compound |
| β-conglycinin or a subunit thereof | Oleosin | No additive compound |
| β-conglycinin or a subunit thereof | Oleosin | At least one additive compound |
| β-conglycinin or a subunit thereof | 90%, 95%, 97% or 99% Sequence Identity to Oleosin | No additive compound |
| β-conglycinin or a subunit thereof | 90%, 95%, 97% or 99% Sequence Identity to Oleosin | At least one additive compound |
| β-conglycinin or a subunit thereof | Low Molecular Weight Fraction of Oleosin | No additive compound |
| β-conglycinin or a subunit thereof | Low Molecular Weight Fraction of Oleosin | At least one additive compound |
| β-conglycinin or a subunit thereof | 17 kDa Fraction | No additive compound |
| β-conglycinin or a subunit thereof | 17 kDa Fraction | At least one additive compound |
| β-conglycinin or a subunit thereof | SEQ ID NOs: 12 or 14 | No additive compound |
| β-conglycinin or a subunit thereof | SEQ ED NOs: 12 or 14 | At least one additive compound |
| β-conglycinin or a subunit thereof | Lipoprotein | No additive compound |
| β-conglycinin or a subunit thereof | Lipoprotein | At least one additive compound |
| β-conglycinin or a subunit thereof | Mammalian Lipoprotein | No additive compound |
| β-conglycinin or a subunit thereof | Mammalian Lipoprotein | At least one additive compound |
| β-conglycinin or a subunit thereof | Egg Yolk Lipoprotein | No additive compound |
| β-conglycinin or a subunit thereof | Egg Yolk Lipoprotein | At least one additive compound |
| β-conglycinin or a subunit thereof | Fat Globule Membrane Protein | No additive compound |
| β-conglycinin or a subunit thereof | Fat Globule Membrane Protein | At least one additive compound |
| At least one of SEQ ID NOs: 2, 3, 4, 5, or 6 | Oleosin | No additive compound |
| At least one of SEQ ID NOs: 2, 3, 4, 5, or 6 | Oleosin | At least one additive compound |
| At least one of SEQ ID NOs: 2, 3, 4, 5, or 6 | 90%, 95%, 97% or 99% Sequence Identity to Oleosin | No additive compound |
| At least one of SEQ ID NOs: 2, 3, 4, 5, or 6 | 90%, 95%, 97% or 99% Sequence Identity to Oleosin | At least one additive compound |
| At least one of SEQ ID NOs: 2, 3, 4, 5, or 6 | Low Molecular Weight Fraction of Oleosin | No additive compound |
| At least one of SEQ ID NOs: 2, 3, 4, 5, or 6 | Low Molecular Weight Fraction of Oleosin | At least one additive compound |
| At least one of SEQ ID NOs: 2, 3, 4, 5, or 6 | 17 kDa Fraction | No additive compound |
| At least one of SEQ ID NOs: 2, 3, 4, 5, or 6 | 17 kDa Fraction | At least one additive compound |
| At least one of SEQ ID NOs: 2, 3, 4, 5, or 6 | SEQ ID NOs: 12 or 14 | No additive compound |
| At least one of SEQ ID NOs: 2, 3, 4, 5, or 6 | SEQ ID NOs: 12 or 14 | At least one additive compound |
| At least one of SEQ ID NOs: 2, 3, 4, 5, or 6 | Lipoprotein | No additive compound |
| At least one of SEQ ID NOs: 2, 3, 4, 5, or 6 | Lipoprotein | At least one additive compound |
| At least one of SEQ ID NOs: 2, 3, 4, 5, or 6 | Mammalian Lipoprotein | No additive compound |
| At least one of SEQ ID NOs: 2, 3, 4, 5, or 6 | Mammalian Lipoprotein | At least one additive compound |
| At least one of SEQ ID NOs: 2, 3, 4, 5, or 6 | Egg Yolk Lipoprotein | No additive compound |
| At least one of SEQ ID NOs: 2, 3, 4, 5, or 6 | Egg Yolk Lipoprotein | At least one additive compound |
| At least one of SEQ ID NOs: 2, 3, 4, 5, or 6 | Fat Globule Membrane Protein | No additive compound |
| At least one of SEQ ID NOs: 2, 3, 4, 5, or 6 | Fat Globule Membrane Protein | At least one additive compound |

In one embodiment of the invention, the composition has an isolated soy material content of not less than 50 weight percent of the composition and an oil body associated protein content of not less than 0.5 weight percent of the composition. More preferably, however, the composition has an isolated soy material content of not less than about 70 to about 90 weight percent weight percent of the composition and an oil body associated protein content of between about 1 to about 5 weight percent of the composition. When present, the additive compounds such as isoflavone or saponin compounds typically comprises not less than 10 mg/100 g of the composition and may further comprise between about 30 to 300 mg/100 g of the composition. Moreover, when present, the additive compounds such as phospholipids or a carbohydrate substantially resistant to digestion, typically comprises not less than 2 weight percent and may further comprise between about 10 to 50 weight percent of the composition.

The compositions of the invention may be administered to a mammal as agents to prevent or treat the development of atherosclerosis and vascular disease. More specifically, the compositions of the invention may be administered to a mammal, preferably a human, to decrease the total serum cholesterol concentration, to decrease the low density lipoprotein concentration, to increase the high density lipoprotein concentration, to decrease the concentration of cholesterol in the liver, and to decrease the concentration of serum triglycerides. Generally speaking, without being bound by any particular theory, it is believed that the compositions of the invention exert their hypocholesterolemic activity by preventing cholesterol absorption, substantially inhibiting bile acid reabsorption, and/or may be utilized as a nitrogen source by bacteria in the colon of the mammal.

IV. Pharmaceutical Compositions and Administration

Any of the compositions of the present invention can be formulated as pharmaceutical or nutritional compositions. Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intratermal injection, or infusion techniques. Formulation of drugs is discussed in, for example, *Remington's Pharmaceutical Sciences*, (1975), and Liberman and Lachman (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include. pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of therapeutically active compounds which are administered and the dosage regimen for treating a cardiovascular disease condition with the compounds and/or compositions of this invention depends on a variety of factors, including the age, weight, sex and medical condition of the subject, the severity of the disease, the route and frequency of administration, and the particular compound employed, and thus may vary widely. Generally acceptable and effective daily doses may be from about 0.1 to about 6000 mg/Kg body weight per day, more typically from 100 about to 2500 about mg/Kg per day, and most preferably from about 200 to about 1200 mg/Kg per day.

The detailed description set-forth above is provided to aid those skilled in the art in practicing the present invention. Even so, this detailed description should not be construed to unduly limit the present invention as modifications and variation in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

V. EXAMPLES

Example 1

Identification of HMF from Soy Protein

The polypeptides present in the HMF of soy protein have active cholesterol-lowering properties (See Example 2). Studies were conducted to identify the origin and partial sequences of these polypeptides. The methods used were as follows:

A. Polyacrylamide Gel Electrophoresis.

Polyacrylimide gel electrophoresis methods were performed in accordance with methods known in the art. Several different methods were employed in the present invention, and are as follows:

B. Tris-Glycine Sodium Dodecylsulfate-Polyacrylamide Gel Electrophoresis (SDS-PAGE)

Prepare soy protein samples for analysis by freezing intact or ground soybeans and powdering them in a percussion mortar (powdering not necessary for soy protein isolates) and extracting proteins for 1 hr at room temperature using 0.03M Tris, 0.01M 2-mercaptoethanol at pH=8.0. Prepare a 4 mg/ml solution of these proteins in SDS solubilizing solution (0.0625 M Tris, 2.3% SDS, 5% β-mercaptoethanol, 10% glycerol, pH 6.8, trace of bromophenol blue as a tracking dye). Heat samples for 10 min at 70° C., cool 5 min, then centrifuge to pellet insoluble materials. Load 5 μL (20 μg) of each sample supernatant on a 10-20% total acrylamide gel (as described by Laemmli (1970) and separate by electrophoresis at 15-30 mA per gel (constant current) or 60-100 volts (constant voltage). Terminate electrophoresis when tracking dye is within 2 mm of the bottom of the gel. SYPRO Orange may be substituted for Coomassie following method number 2 in Malone et al, (2001).

C. SDS-PAGE Analysis by NuPAGE Gel Electrophoresis

Prepare samples as detailed in Tris Glycine SDS-PAGE section, using 4×NuPAGE LDS Sample Buffer (NOVEX catalog # NP0003 as ¼ of the sample volume, and 500 mM dithiothreitol as 1/10 of the sample volume. Load 4 μL (16 μg) of each sample supernatant on a Novex 4-12% acrylamide Bis-Tris gel. Fill Novex Xcell 2 mini-gel tank with NUPAGE MES Running Buffer (50 mM MES, 50 mM Tris, 3.5 mM SDS, 1.025 mM EDTA, pH=7.7) and separate proteins by electrophoresis at 200 volts (constant voltage) until the tracking dye reaches the slot at the bottom of the gel. Stain gel as detailed in Tris-Glycine SDS-PAGE protocol.

D. 2-D PAGE of Soy Proteins

Extract soy proteins as detailed in Tris-Glycine SDS-PAGE section. Supplement samples to contain 8M urea, 2% CHAPS, 0.35% dithiothreitol, 0.2% ampholyte, and 15% isopropanol to a final volume of 450 μL containing 0.6 to 1.05 mg total protein. Use 430 μL of this solution to re-swell an 18 cm pH 3-10 immobilized pH Gradient (IPG) drystrip for 24-30 hrs (cover strips with mineral oil while re-swelling). Using water-soaked electrode strips, focus the IPG strips (covered with mineral oil) for 50,000-70,000 volt-hours using the following voltage ramping approach. Begin with 1 hr at 100 volts (v), then 1 hr at 200 v, 2 hrs at 400 v, 14 hrs in a linear ramp from 400 to 10000 volts, then up to 48 hrs at 10000 volts to reach the final volt-hour total. Soak each IPG strip in 1.5 mL of sample equilibration solution (62.5 mM Tris, 2.3% SDS, 5% 2-mercaptoethanol, pH 6.8 and a trace of bromophenol blue as a tracking dye) for 3.5 min. Drain strips, then place each on a 10-20% acrylamide Tris Glycine gel, sealing it in place using hot 1% agarose in equilibration solution. Run the second dimension gels and stain them as detailed in the Tris-Glycine SDS-PAGE section.

E. In Situ Trypsinization of Proteins in Acrylamide Gels

Cut out gel bands or spots, placing them in 1500 μl siliconized microcentrifuge tubes. Wash twice with 50% methanol (30 min per wash) to remove stain. Equilibrate gel pieces in 50% acetonitrile (in 200 mM ammonium acetate pH=8.0) for 15 min. Repeat washes twice. Wash 15 min 100% acetonitrile, then evaporate to dryness in a Speedvac. Trypsinize for 16-20 hrs at 37° C. using 20 μg/mL sequencing grade modified trypsin (Promega cat # V5111) in 10% acetonitrile in 200 mM ammonium acetate pH-8.0. Extract peptides with 50% acetonitrile, 0.1% trifluoroacetic acid (TFA) for 20 min agitating with a Nutator. Repeat extraction using 80% acetonitrile 0.1% TFA in ammonium acetate for 20 min. Repeat the last extraction for 30 min. Combine all supernatents and dry extracts in Speed-vac.

F. Trypsinization of the Bands to Provide Tryptic Polypeptides of the Polypeptides Present in a Given Band.

In gel trypsin digestion of the bands in order to provide tryptic polypeptides of the polypeptides present in a given band was performed according to the following protocol:
1) Cut out gel spots, making the largest dimension of any piece less than 1 mm. Place gel pieces in 1500 μl siliconized microcentrifuge tubes.
2) Wash gel pieces with 2 or more washes (200 μl per tube) of 50% methanol (30 min per wash) to remove stain. Coomassie stained gels may be washed additional times to remove stain. Gel pieces may be stored in this solution. Agitate tubes using Nutator.
3) Wash gel pieces twice in 200 μl 50% acetonitrile (in 200 mM ammonium acetate pH=8.0—adjusted with NH4OH) for 15 min per wash, then one additional wash for 30 min. Agitate using Nutator.
4) Wash 15 min 100% acetonitrile.
5) Withdraw solution from gel pieces and evaporate to dryness in Speedvac (15 min).
6) Make Trypsin stock by adding 1 ml of 10% acetonitrile (in 200 mM NH4Ac, pH 7.8-8.3—adjusted with NH4OH) to a 20 μg vial of trypsin. (Promega Sequencing Grade Modified Trypsin—cat# V5111 used).
7) Digest protein by adding just enough trypsin solution to cover gel pieces in each tube. Typically, 20 μl is sufficient.
8) Incubate pieces at 37° C. for 16-20 hrs.
9) Cool tubes to room temperature, and microcentrifuge tubes to bring moisture to bottom.
10) Extract peptides with 200 μl 50% acetonitrile, 0.1% trifluoroacetic acid (TFA) for 20 min agitating with a Nutator.
11) Save supernatents individually for each tube, then re-extract using 200 μl 80% acetonitrile, 0.1% TFA for 15 min agitating with a Nutator.
12) Save supernatents adding to that saved previously for each tube, then extract one final time using 200 μl 80% acetonitrile, 0.1% TFA for 30 min with agitation on a Nutator.
13) Save supernatent and add to that saved previously for each tube. Dry extracts in Speed-vac.

G. MALDI-TOF Analysis

Tryptic polypeptides from a band were ionized using laser desorption (for MALDI) or electrospray (for LC/MS and LC/MS/MS) to create a mass spectrum. The masses of the peptides are measured as a mixture using MALDI; there is no separation of the tryptic peptides. Samples were prepared for MALDI analysis using a slightly modified published procedure (Shevchenko et al., 1996). The samples were reconstituted by adding 10 μL 0.1% TFA to each tube containing the dried peptides. Matrix was prepared by dissolving 10 mg/mL nitrocellulose and 20 mg/mL α-cyano-4-hydroxycinnamic acid of a 1:1 (v:v) mixture of acetone and isopropyl alcohol. Matrix was spotted by delivering 0.5 μL of matrix solution onto the MALDI plate. Similarly, 1 μL of sample from each sample was deposited onto the spotted matrix. The sample was allowed to dry on the matrix for approximately 10 min to ensure that peptides bound to the nitrocellulose. Finally, three aqueous washes were performed by depositing 5 μL of 5% formic acid onto each spot and immediately aspirating this solution off using a vacuum line. The MALDI sample plate was then moved to the mass spectrometer for MALDI mass spectrometry analysis. The data was collected using the Voyager DE-STR (Perseptive Biosystems, Framingham, Mass.) in the reflectron mode. The spectra were internally calibrated using known trypsin autolysis peaks. Peak lists of the tryptic peptide masses were generated, and these were searched against the NCBI non-redundant protein sequence database using the MS-Fit search tool in order to identify the proteins (Clauser et al., (1999).

Sometimes, the match is "borderline" and requires confirmation, or the data is weak or there is simply no significant match. In these cases, nano LC/MS/MS is used. In this method, the digest mixture is injected onto a reversed-phase column so that the peptides are separated and introduced into the mass spectrometer (in this case an electrospray, tandem mass spectrometer), one at a time (or at least a couple at a time). The mass spectrometer measures the mass of the peptides, isolates the most abundant ones by filtering out everything else, and sends a peptide into a collision cell where the peptide collides with Ar gas. Peptides tend to fragment about the amide bonds, so the fragments can be indicative of the amino acid sequence. The fragmentation data can be submitted to a database searching tool, which matches the data to the protein sequence database. It uses the partial sequence and the original mass of the tryptic peptide to get a match. A protein can be identified using the MS/MS data from a single tryptic peptide with high confidence.

H. Nano HPLC

Nano HPLC is used to separate the tryptic fragments from a purified protein (purified by electrophoresis) so that only one (or a few) peptides are introduced into the electrospray, tandem mass spectrometer at a time. Samples were injected into a CapLC (Waters, Milford, Mass.) system equipped with an autosampler, gradient and auxiliary pump. Five microliters was injected via "microliter pickup" mode and desalted on-line through a 300 μm×5 mm $C_{18}$ trapping cartridge (LC Packings, San Francisco, Calif.). The samples were desalted at high flow (30 μL/min) for 3 min. The peptides were separated on a 100 μm×150 mm Magic $C_{18}$ column (Michrom BioResources, Auburn, Calif.) prior to introduction into the mass spectrometer. A typical reverse phase gradient was used from low to high organic over about 30 min. Mobile phase A was 0.1% formic acid and B was 100% acetonitrile, 0.1% formic acid. The flow rate was also increased linearly with organic mobile phase. The system utilized a small split flow resulting in a column flow rate of approximately 300-700 nL min.

I. MS/MS Analysis and Data Processing

For LC/MS/MS, there is a separation step (reversed-phase LC), so that the tryptic peptides are introduced into the mass spectrometer (ideally) one at a time. It is called MS/MS, or tandem MS, because first the mass of a peptide is measured, and then the mass of the fragments from this peptide are measured. A tryptic peptide is fragmented by collisions with a stationary gas (Ar) and the masses of the fragments are measured. This will often give the sequence of at least part of the peptide. Data dependent MS/MS studies were performed on a Q-Tof mass spectrometer (Micromass, Beverly, Mass.). The inlet is a modified nanospray source designed to hold a picotip (New Objective, Cambridge, Mass.). The collision energy used for CAD was determined based on the mass and charge state of the peptide. The data was processed by ProteinLynx version 3.4 (Micromass, Beverly, Mass.) to generate peak list files. The data was searched against the NCBI non-redundant protein sequence database using the search engine MASCOT (Matrix Science, London, UK). The search engine reported the top twenty hits. Sequence data that did not match any entries in this database were searched against the dbEST database from NCBI as well as internally generated sequence databases.

J. Study 1

HMF from the soy protein isolate called OBAP-rich was separated using polyacrylimide gel electrophoresis. Five polypeptide containing bands or areas of the gel were trypsinized and analyzed for amino acid sequence using mass spectroscopy (FIG. 7). The origins of the bands were identified as in Table 2:

TABLE 2

| Band | Protein Identification | Comments |
|---|---|---|
| A | Glycinin AlaBx (72296) | Automated match, two sequences* |
| B | Glycinin G1 (99907) | Automated match, three sequences* |
| C | dbEst annotated as putative oleosin | Sequence: YETNSSLNNPPSR (SEQ ID NO:10) |
| D | Alpha subunit beta-conglycinin (72289) | Many peptides |
| E | Alpha subunit beta-conglycinin (72289) | Many peptides - many in common with other subunits of beta-conglycinin. |

*Glycinin sequences line up together to make residues 401-435 of the basic subunit of G1 glycinins (72296, AlaBx precursor) (SEQ ID NO:1) (VFDGELQEGRVLIVPQNFVVAARSQSDNFEYVSFK) (SEQ ID NO:1):
A  VFDGELQEGR and SQSDNFEYVSFK
B  Same two as in A plus: VLIVPQNFVVAAR

K Study 2

Figure 8:
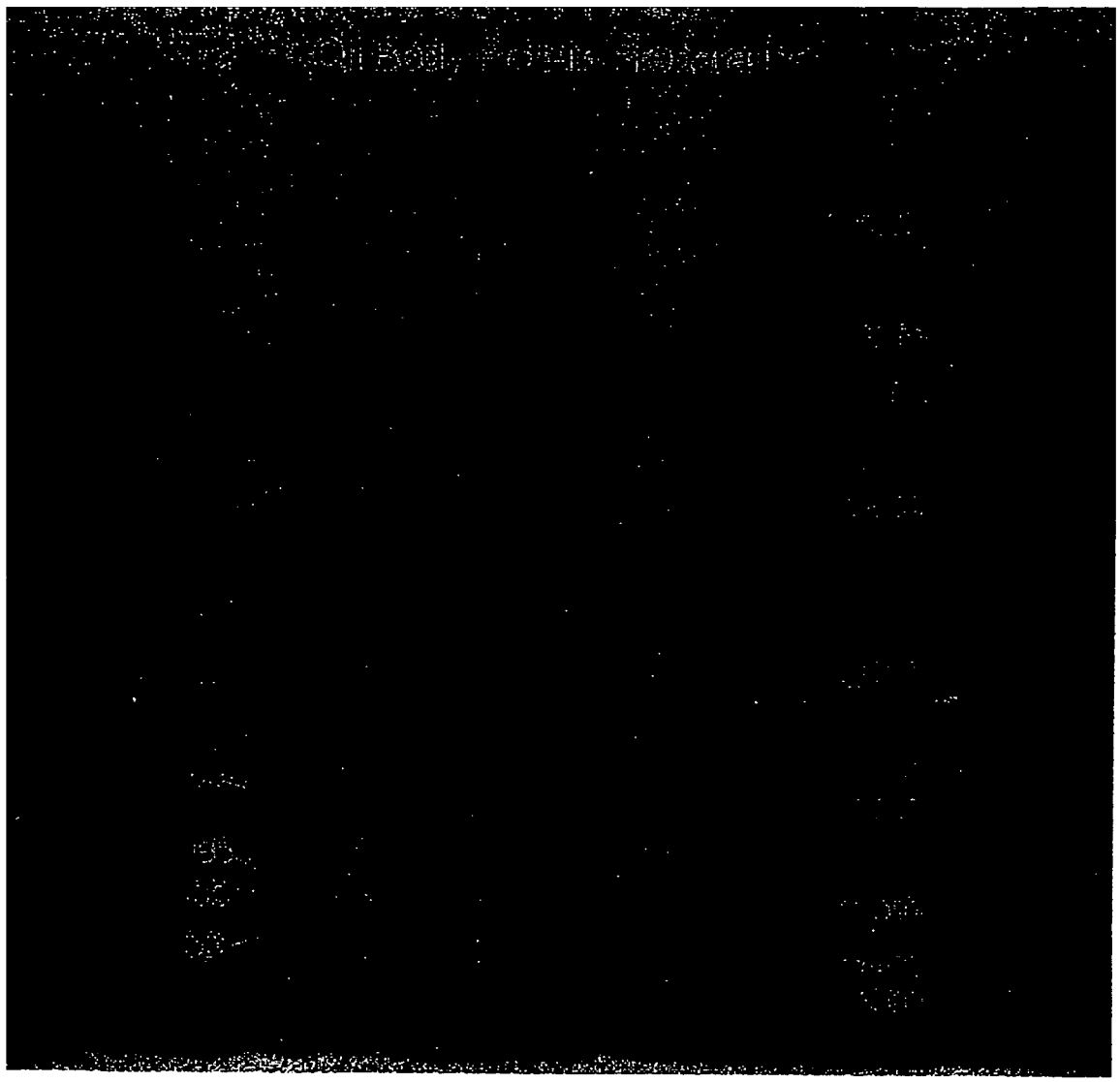
FIG. 8 depicts oil body associated proteins (P34 and oleosins) purified and separated on a polyacrylimide gel.

The putative oleosin sequence above did not match known oleosin sequences. The sequence of the lower molecular weight soy oleosin (~18 kDa) was not known. The purpose of the following study was to determine if the above "putative oleosin" sequence was from the 18 kDa soybean oleosin. Oil-body-associated proteins (p34 protein and oleosins) were purified and separated on a polyacrylimide gel (FIG. 8). The bands were trypsinized and analysed by MS.

The presence of a tryptic peptide, released from the amphipathic N-terminal region of oleosin right next to the hydrophobic domain, was confirmed in a 12 kDa band isolated from HMF. The average mass per amino acid is 111.1 Daltons. Thus, the number of amino acids in a 12 kDa peptide is approximately 108 amino acids. Therefore, the peptide found in HMF must also contain a portion of the hydrophobic domain of oleosin. Sequence YETNNSSLNNPPSR (SEQ ID NO:10) represents residues 33-45 of the putative oleosin which falls just before the beginning of the hydrophobic core region of the protein.

Results: Confirmed that sequence, YETNSSLNNPPSR (SEQ ID NO:10), is found in low molecular weight soy oleosin.

TABLE 3

| Band | Protein Identification | Comments |
|---|---|---|
| AA | Probable thiol protease precursor | One peptide confirmed |
| BB | P24 oleosin isoform A (P89) | Multiple peptides hit gi1709459 (A) |
| CC | P24 Oleosin isoform B (P91) or A (P89) | Multiple peptides hit gi266689 (B) & gi1709459 (A) |
| DD | Low molecular weight (16-24 kD)oleosin | Two peptides confirmed: (T)YETNSSLNNP(P), (R) AkdYGSYA (Q), Many internal ESTs hit. |

L. Study 3

Figure 9:
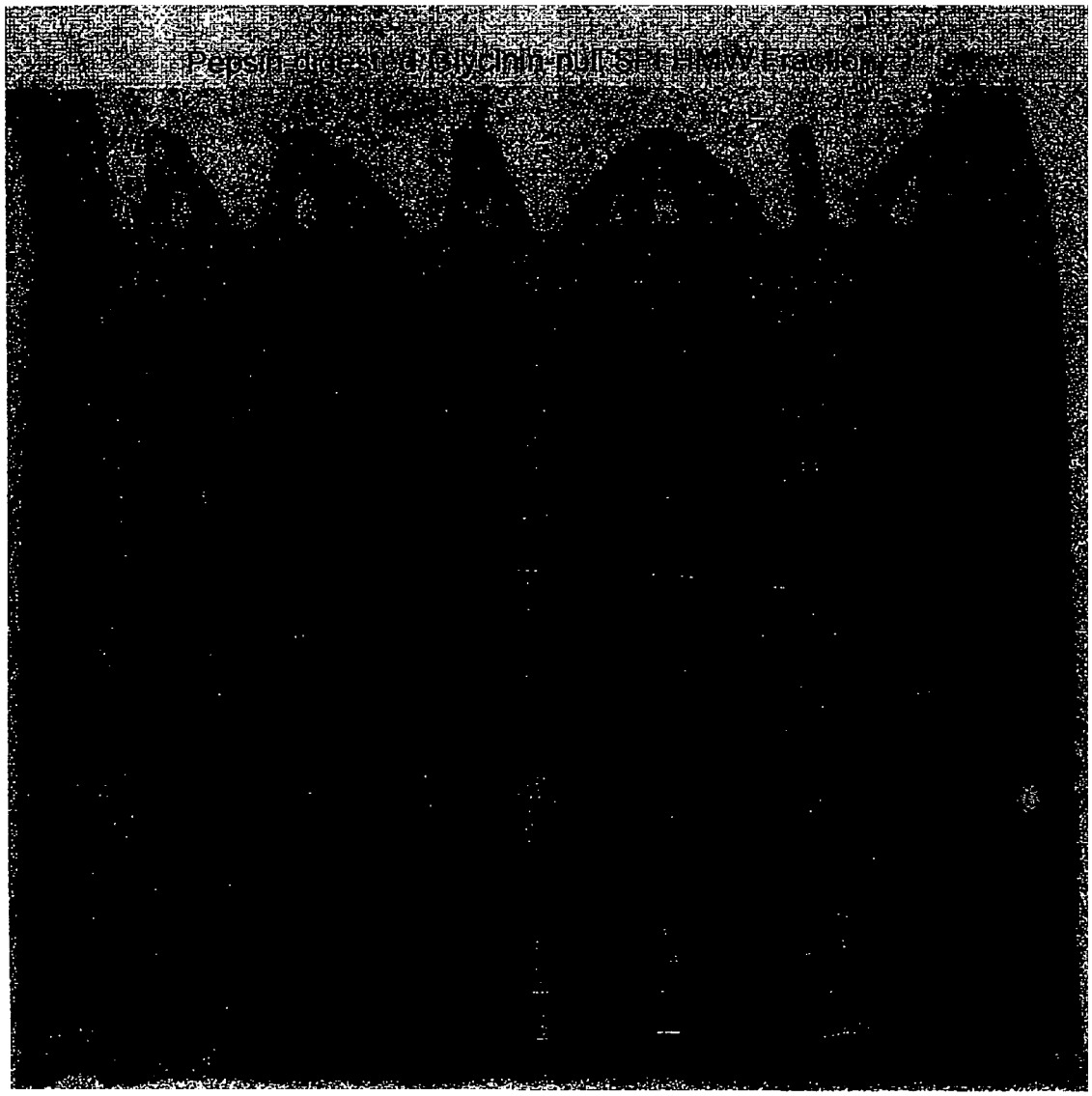
FIG. 9 depicts a gel containing HMF from pepsin digested soy protein isolate produced from soybeans lacking G1 glycinins.

The HMF characterized in Study 1 was made from a soy protein fraction which had little beta-conglycinin. This helped identify the glycinin subunits which are present in HMF. The following study was conducted to determine what, if any, beta-conglycinin sequences can be identified in HMF. Soybeans lacking G1 glycinins were used to make soy protein isolate and the isolate was digested with pepsin to make HMF. The HMF was separated using polyacrylimide gel electrophoresis (FIG. 9) and the bands were trypsinized and characterized using MS.

Results: Polypeptide sequences from beta-conglycinins were identified.

TABLE 4

| Band | Protein identification from MALDI |
|---|---|
| A1 | Beta subunit of beta-conglycinin |
| A2 | same as A1 |
| A3 | Alpha or alpha-prime subunit of beta-conglycinin* |
| A4 | Same peptides as A3 |
| A5 | Same peptides as A3 |
| A6 | Same peptides as A3 |

*Precursor alpha-prime beta-conglycinin (121286):
QNPSHNKCLR (SEQ ID NO:18) and sequences in 4191814 listed below.
*Alpha-prime subunit of beta-conglycinin (4191814):
NQYGHVR (SEQ ID NO:6), and sequences in 7442025 listed below.
*Alpha-subunit of beta-conglycinin (7442025):
NILEASYDTKFEEINK (SEQ ID NO:8), LQESVIVEISKK (SEQ ID NO:4), QQQEEQPLEVRK (SEQ ID NO:5)

Example 2

Effect of HMF on Cholesterol Uptake

Caco-2 cell line is derived from a human colorectal carcinoma and is commonly used to study intestinal epithelial cell physiology. These cells have been used to study cholesterol, glucose, amino acid, vitamin, fatty acid, bile acid and drug transport processes (Hidalgo et al., 1989); Artursson, 1990; Homan and Hamelehle, 1998). These cells express lipid and sterol metabolizing enzymes and transport proteins that are regulated similarly to those in enterocytes (Levy et al., 1995). Also, they are known to express SR-B1, a recently identified protein that may play a role in cholesterol absorption (Werder et al., 2001) as well as various proteins in the ATP-binding cassette transporter family which may also play a role in mediating net cholesterol uptake by intestinal epithelial cells (Taipalensuu et al., 2001).

Soy protein is the source of HMF. Briefly, soy proteins were incubated with pepsin for 17 hrs (0.2% NaCl in aqueous phase, 38° C., pH 1.1, pepsin was 5% of soy protein isolate), heat-treated for 20 min at 90° C. to inactivate pepsin, cooled on ice, adjusted pH to 6.21 with 0.2 M $Na_2CO_3$ and centrifuged at 4,500 g for 20 min. This pellet is washed 3 times with water and identified as HMF.

A. Culture of Caco-2 Cells for Cholesterol Absorption Assays
1. Pre-coat 96-well Costar solid white tissue-culture treated plates (Costar #3917) with rat tail collagen as follows:
a) Prepare 20 μg/ml rat tail collagen solution (Becton Dickinson/Collaborative Biomedical Products Cat. # 40236) in 0.02 N acetic acid:
0.02 N Acetic Acid: Add 11.5 ml of 17.4 N Acetic Acid/10 m sterile $H_2O$ Add 60 μl of collagen (3.32 mg/ml) per 10 ml of 0.02 N Acetic Acid
b) Add 250 μl of collagen solution/well for a 96 well plate and allow to remain at room temperature overnight in laminar hood
c) Rinse each well 1×250 μl of DMEM followed by a rinse with 100 ml of DMEM
2. Rinse 2 T-150 flasks (Costart #430825) of Caco-2 cells at 70-80% confluence (use cells with a passage number between 41 and 60) with 10 ml Dulbeco's Phosphate buffered saline without $Ca^{2+}$ and $Mgt^{2+}$.
3. Add 6 ml of 0.25% Trypsin/EDTA solution to each flask and incubate for 5-10 min at 37° C.
4. Use 10 ml pipette to wash cells off of the T-150 flask and to break up cell clumps. Transfer cell suspension to a 50 ml tube.
5. Add 12 ml of complete medium DMEM with 10% fetal bovine serum, 1× Non-essential amino acids, 50 mg/ml gentamicin to the cell suspension, mix and pellet cells by centrifugation for 5 min at 2000 rpm (Sorvall RT7).
6. Remove media and replace with 20 ml of complete media. Use 10 ml pipette to disperse cells. [2×T150 flasks~80% confluent generates~$10 \times 10^6$ cells].
7. Plate the cells into the 96 well collagen-coated microtiter plates at a density of 3200 cells/100 μl per well.
8. Feed cells on alternate days with complete medium. Cells will express the surface receptors necessary for cholesterol absorption 13 days post plating.

B. Cholesterol Absorption Assay
Uptake of micellar cholesterol by Caco-2 cells was conducted by a modification of the method reported by Field et al. (1991). Our method is described as follows:
1. Compounds/peptides to be tested for their ability to inhibit cholesterol absorption in Caco-2 cells are dissolved as stock solutions in DMSO. Dilutions of test compounds from STOCK solutions are made in pentanol. Dilutions of compounds to be used in the Caco-2 cholesterol absorption inhibition assay should be 10× higher than the desired final dilution to be assayed, i.e pipet 2 mM solution in well to get 200 μM final in assay. Sitostanol is used as the control cholesterol absorption inhibitor with maximal inhibition at 200 mM (0% cholesterol absorption control). Solvent only is used as the 100% cholesterol absorption (high dpm).
2. Dilutions of control and test compounds/peptides are pipetted into polypropylene shallow-well microtiter plates (Sigma M-4029) in triplicate.
3. The plates are dried in a GeneVac instrument overnight at a temperature of 35° C.-45° C. Plates are checked for complete dryness before next step.
4. The $^3$H-cholesterol micelle mix is prepared as follows in Trace-Clean amber vials with septa liner caps (VWR Cat. No. 15900-036):
To 1.0 ml of 10× STOCK micelle solution (10× Stock Micelle Solution=50 mM Taurocholate, 1 mM Oleic Acid, 1 mM Cholesterol) add 37.5 μl $^3$H-Cholesterol (NEN Cat. No. NET-725) (0.75 nmol chol)=37.5 μCi $^3$H-cholesterol (Solution contains 0.075% chol as radiolabel=trace). Prepare 1.8 ml per microtiter assay plate to allow for overage.
5. Pipet 15 μl/well of diluent $CH_3Cl$:MeOH (1:1) into all wells of the dried plates to solvate the dried residue. Use the polypropylene reservoirs for this and keep reservoirs on ice to minimize evaporation of the solvent.
6. To the same plates, add 15 μl of the $^3$H-cholesterol mix to each well using a polypropylene reservoir on ice to contain the radiolabel solution.
7. Dry the plates in a pre-heated 37° C. evaporation chamber (VWR) flushing with nitrogen gas for approx. 20-30 mins.
8. Rinse dried wells with 50 μl/well of ethyl ether and re-dry in evaporation chamber. Repeat ether rinse 1 more time and dry.

9. Place plates in vacuum dessicator overnight.
10. Pipet 150 μl room temperature Hank's Balanced Salt Solution (HBSS) (Sigma H-8264) into each dried well using a Quadra 96 workstation. The final concentration of micellar lipids is as follows: 5 mM taurocholate, 100 μM oleic acid, 100 μM cholesterol and 3.75 μCi/ml $^3$H-cholesterol (or approx. 5 μM).
11. Seal plates with adhesive sealing tape (Packard TopSeal-A Adhesive Sealing Tape or Sigma Mylar Sealing Tape T-2162) and shake on Labline plate shaker, Model 4625, (setting=6) for at least 30 mins at room temperature to solubilize micelles.
12. Wash Caco-2 cells plated on 96 well plates (described above) 5 times with HBSS using automated cell washer. Do this JUST PRIOR to step 13. Remove any excess liquid by smacking plate on paper towels before adding the micelles in the next step.
13. Transfer 100 μl of solubilized micelles into the appropriately marked Caco-2 cell plate using the Quadra 96 workstation. Place the plate back in the 37° C. incubator for 4 hr.
14. Wash cells 5 times with cold 1 mM Taurocholate in HBSS (1 mM TC) using automated cell washer.
15. Pipet 200 μl/well of scintillation cocktail (Packard MicroScint 40, Cat. No. 6013641) into cell plates using Quadra 96 workstation.
16. Seal plates with heat sealing tape (Packard TopSeal-S Heat Sealing Film) and shake the plates (setting=6 at least) for at least 20 mins to mix the fluor with the cell samples.
17. Keep the plates in the dark overnight.
18. Count the dpm using a Packard TopCount NXT instrument.
19. Results are calculated as % of Control (no inhibitor) as follows:

$$\% \text{ of Control} = \frac{\text{Test compound/peptide dpm} - 200 \, \mu\text{M sitostanol dpm}}{\text{Control (no compound) dpm} - 200 \, \mu\text{M sitostanol dpm}} \times 100$$

Figure 10:
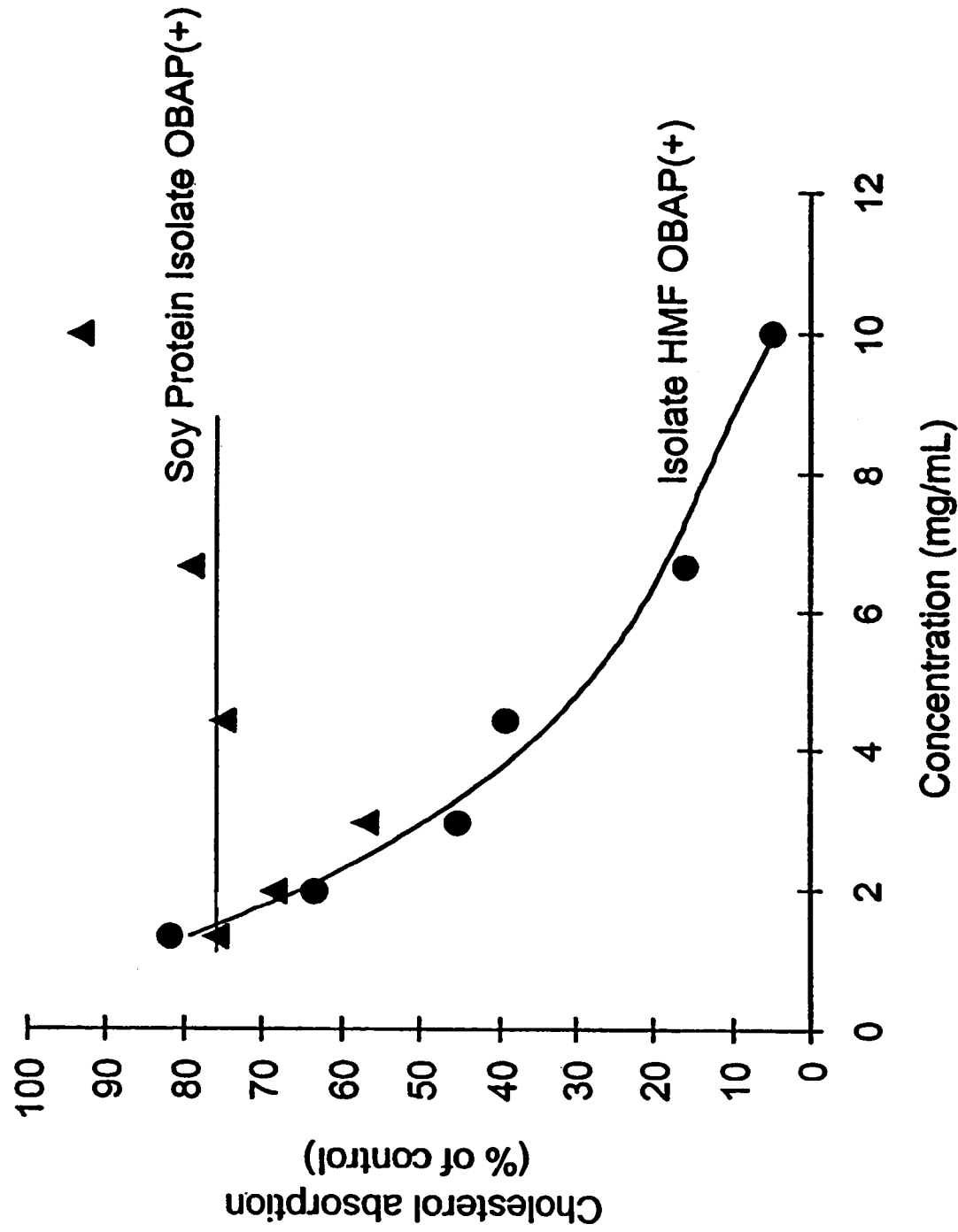
FIG. 10 depicts a graph illustrating the dose dependent inhibition of cholesterol uptake by Caco-2 cells of isolate HMF from OBAP(+) versus OBAP(−) soy protein isolate.

Soy HMF from various sources illustrated a dose-dependent inhibition of cholesterol uptake by Caco-2 cells (For example, see FIG. 10). The concentrations of HMF required to reduce the cholesterol uptake by 50% were between 1.2 and 2.9 mg/mL, with the exception of the beta-conglycinin test (4.7 mg/mL).

Example 3

Molecular Pharmacological Characterization of HMF's Mechanism of Action

To determine whether test compounds/peptides affected the solubility of $^3$H-cholesterol into the micellar solutions prepared for the cholesterol absorption assay (see Methods for Example 2), the following assay was performed:
1. Micelles are prepared as described in Methods to Example 2, up to and including step #11.
2. Transfer 20 μl of solubilized micelles into opaque Costar plates (Costar #3917) using the Quadra 96 workstation.
3. Pipet 200 μl/well of scintillation cocktail (Packard MicroScint 40, cat. No. 6013641) into microtiter plate wells using Quadra 96 workstation.
4. Seal plates with heat sealing tape (Packard TopSeal-S Heat Sealing Film) and shake the plates (setting=6 at least) for at least 20 mins to mix the fluor with the micelle samples.
5. Keep the plates in the dark overnight.
6. Count the dpm using a Packard TopCount NXT instrument.
7. Results are calculated as % of Control (no inhibitor) as follows:

$$\% \text{ of Control} = \frac{\text{Test compound/peptide dpm} - 200 \, \mu\text{M sitostanol dpm}}{\text{Control (no compound) dpm} - 200 \, \mu\text{M sitostanol dpm}} \times 100$$

8. If a test compound/peptide displaces $^3$H-cholesterol from the micelles, a decrease in the test compound/peptide dpm will be seen with higher concentrations of test compound/peptide. If not, the dpms in the solublized micelles should remain fairly constant over the range of dilutions of test compound/peptide tested.

Figure 11:
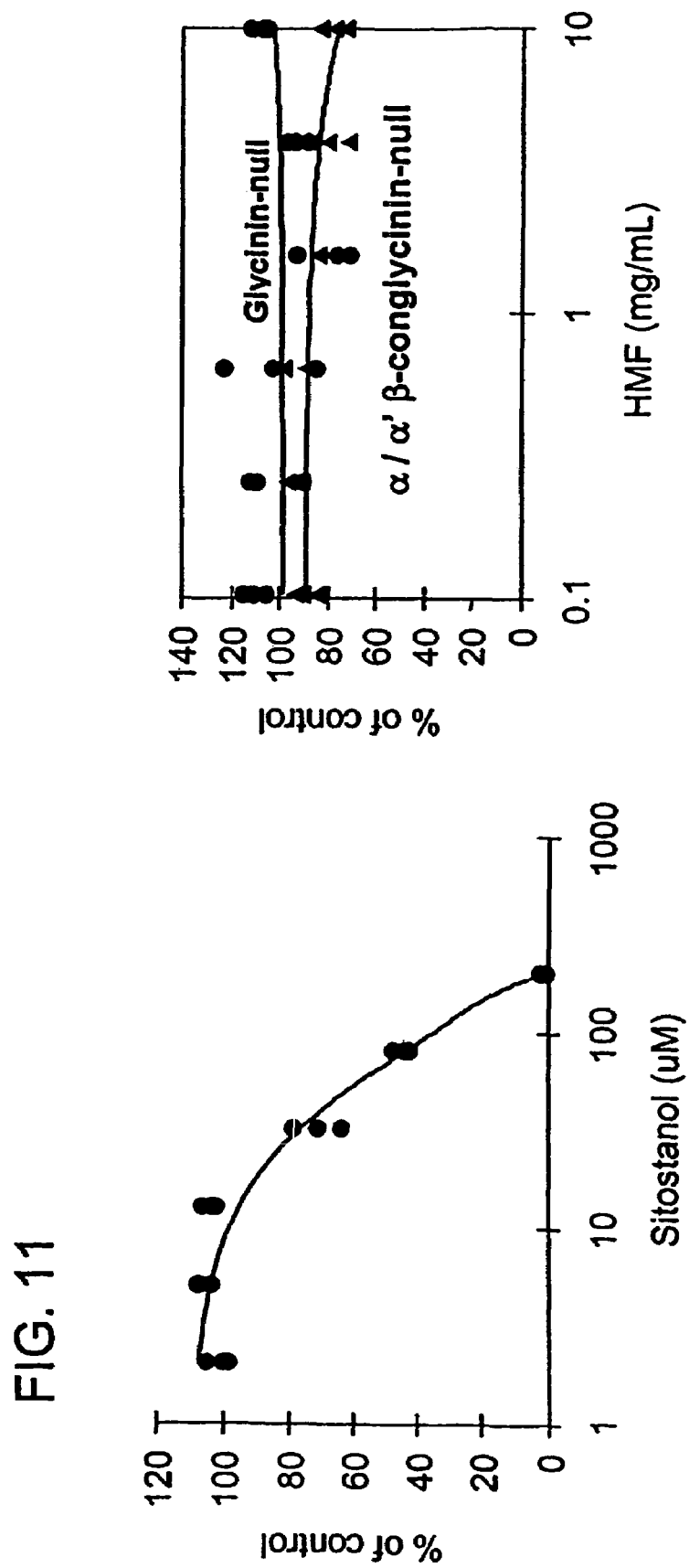
FIG. 11 depicts graphs illustrating the difference between the cholesterol absorption in the presence of sitostanol versus cholesterol absorption in the presence of glycinin-null and α/α' β-conglycinin-null HMF, thereby demonstrating the difference in mechanisms.

FIG. 11 illustrates that this is in contrast to the primary mechanism of cholesterol inhibition by sitostanol.

Example 4

Characterization of Soy Protein HMF

Comparisons were made of the yield of HMF from soy protein isolate fractions which have low amounts of oil body associated protein (OBAP(−)), a fraction rich in oil body associated protein (OBAP(+)) and a control. All were made from the same soybeans (variety A2247).

Briefly, fractions of soy proteins were incubated with pepsin for 17 hrs (0.2% NaCl in aqueous phase, 38° C., pH 1.4, pepsin was 5% of soy protein isolate), heat-treated for 20 min at 90° C. to inactivate pepsin, cooled on ice, pH adjusted to 6.21 with 0.2M Na$_2$CO$_3$ and centrifuged at 4,500 g for 20 min. The pellet was washed 2 times with water and freeze dried. The weight of the dry pellet was compared to the weight of the original amount of soy protein isolate used in the assay to determine yield of HM [(final weight/initial weight)×100]. The OBAP(+) and control soy protein samples both produced HMF. However, the OBAP(−) fraction did not yield any HMF, indicating that oleosin and or components associated with oleosin (e.g. saponins, phospholipids) control the digestibility of the soy proteins.

The following are the procedures utilized to fractionate soy proteins into soy protein isolates (SPI):

A. Procedure 1: OBAP(−)
1. Add 1 kg defatted soy flakes (from Cargill) into 15 kg of DI water. Adjust the pH to 7.5 with 1N NaOH. Mixing at room temperature for one hour.
2. Centrifuge the mixture at 10,000 g for 10 min and collect the supernatant.
3. Add Na$_2$SO$_4$ and CaCl$_2$ into the supernatant at a concentration of 30 mM, respectively.
4. Adjust the pH of the supernatant from step 3 to pH 2.8 with 2N HCl. Centrifuge the mixture at 10,000 g for 10 min. Collect the supernatant.
5. Dilute the supernatant (from step 4) with DI water by 4 times (e.g., from 1 L to 4 L). Adjust the pH to 4.5 with 2N NaOH. Centrifuge at 10,000 g for 10 min. Collect the precipitate.
6. Redissolve the precipitate from step 5 into DI water and adjust the pH to 7.5 with 2N NaOH.
7. Spray drying the neutralized protein mixture at inlet temperature=200° C., outlet temperature=90-95° C.

B. Procedure 2: OBAP(+)
1. Add 1 kg defatted soy flakes (from Cargill) into 15 kg of DI water. Adjust the pH to 7.5 with 1N NaOH. Mixing at room temperature for one hour.
2. Centrifuge the mixture at 10,0008 for 10 min and collect the supernatant.
3. Add $Na_2SO_4$ and $CaCl_2$ into the supernatant at a concentration of 30 mM, respectively.
4. Adjust the pH of the supernatant from step 3 to pH 2.8 with 2N HCl. Centrifuge the mixture at 10,0008 for 10 min. Collect the precipitate.
5. Redissolve the precipitate from step 4 into DI water and adjust the pH to 7.5 with 2N NaOH.
6. Spray drying the neutralized protein mixture at inlet temperature 200° C., outlet temperature=90-95° C.

C. Procedure 3: Control
1. Add 1 kg defatted soy flakes (from Cargill) into 15 kg of DI water. Adjust the pH to 7.5 with 1N NaOH. Mixing at room temperature for one hour.
2. Centrifuge the mixture at 10,000 g for 10 min and collect the supernatant.
3. Dilute the supernatant (from step 2) with DI water by 4 times (e.g., from 1 L to 4 L). Adjust the pH to 4.5 with 2N HCl. Centrifuge at 10,000 g for 10 min. Collect the precipitate.
4. Redissolve the precipitate from step 5 into DI water and adjust the pH to 7.5 with 2N NaOH.
5. Spray drying the neutralized protein mixture at inlet temperature=200° C., outlet temperature=90-95° C.

In one study, the total protein contents of the samples were, OBAP(−) (94.8%), OBAP(+) (91.8%) and control (68%) (Official Methods of Analysis of the AOAC, 16th Edition, 1995, 990.02, Locator #4.2.08). The yield of HMF from each fraction was determined. Results demonstrated that no HMF was yielded from the OBAP(−) sample (see Table 5). This study indicated the importance of OBAP and/or the importance of the phospholipids, isoflavones and saponins associated with this fraction in obtaining HMF, even though oil body associated proteins do not make up a large portion of the HMF.

In the same study, the trypsin inhibitor activities of the OBAP(−), OBAP(+), and control soy protein isolates were 24, 31.5 and 47.5 TIU/mg, respectively (using a standard AACC method, 1995, 9th edition, method 71-10). These activities do not correlate with the yield of HMF from the samples; thus, eliminating the likelihood that the lack of trypsin inhibitor activity in OBAP(−) isolates caused the lack of HMF formation.

The chymotrypsin inhibitor activities of soy protein samples also did not correlate with the yield of HMF from the samples (Table 5) (AACC, 10th edition, method 22-40).

TABLE 5

Chymotrypsin inhibition units per mg sample and yield of HMF.

|  | CTIU/mg | HMF Yield M |
|---|---|---|
| Glycinin | 2.0 | 5 |
| Beta-conglycnin | 2.3 | 14 |
| OBAP(−) | 5.2 | 0 |
| BC-null | 8.8 | 8 |
| Intermediate | 9.2 | 24 |
| OBAP (+) | 24.5 | 8 |
| Glycinin-null | 39.2 | 19 |

Other soybean fractions were also obtained (glycinin, beta-conglycinin, intermediate) prepared at Iowa State University's pilot plant (15 kg pilot plant process #2; Wu et al., 1999).

Figure 12:
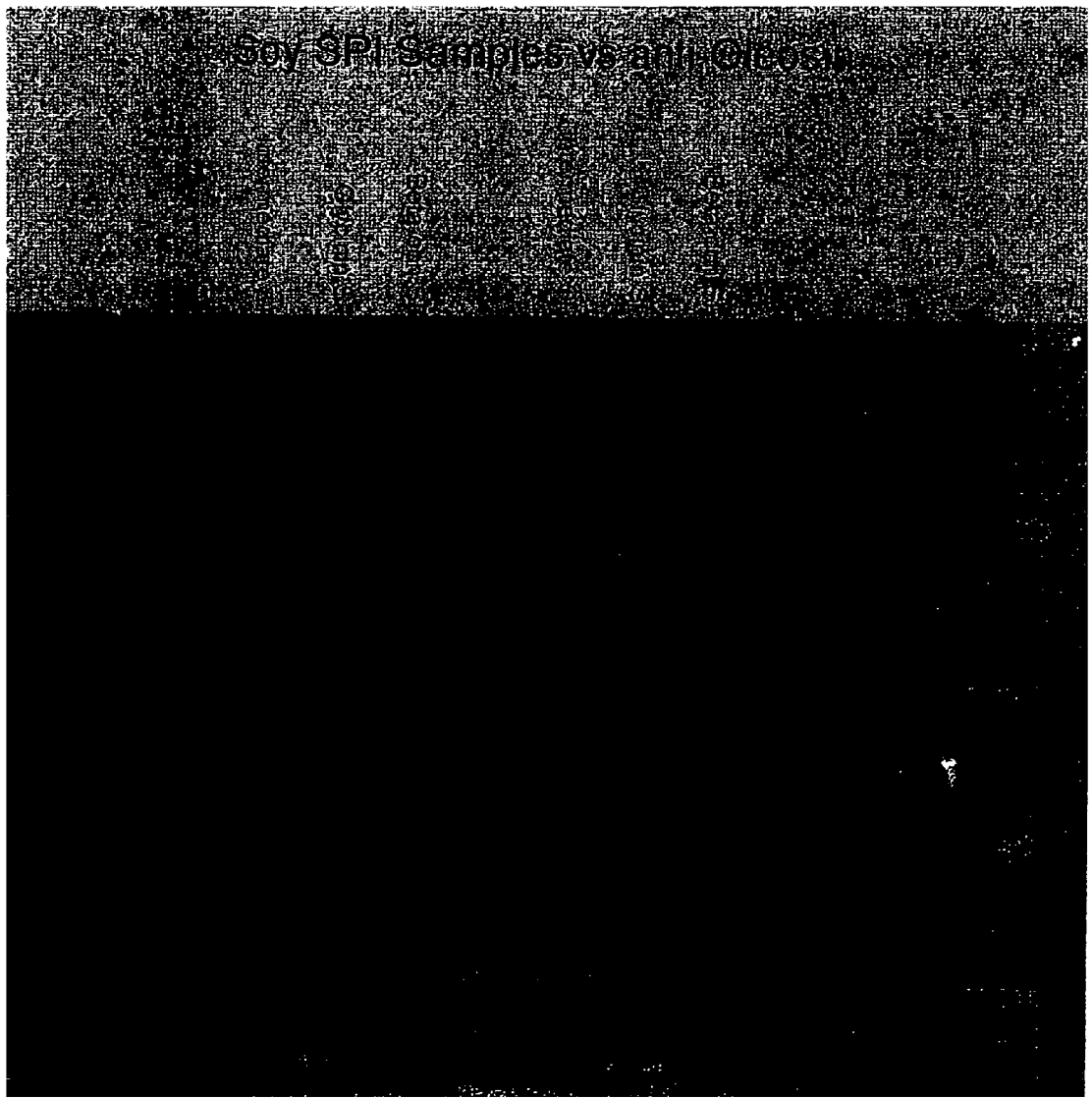
FIG. 12 depicts a gel illustrating the presence of oleosin in each of the samples.

The amount of oleosin in these samples was also determined by Western blotting using an oleosin antibody (See FIG. 12). Again, it was demonstrated that the samples with higher amounts of oleosin produced much higher yields of HMF (Table 6).

Figure 13:
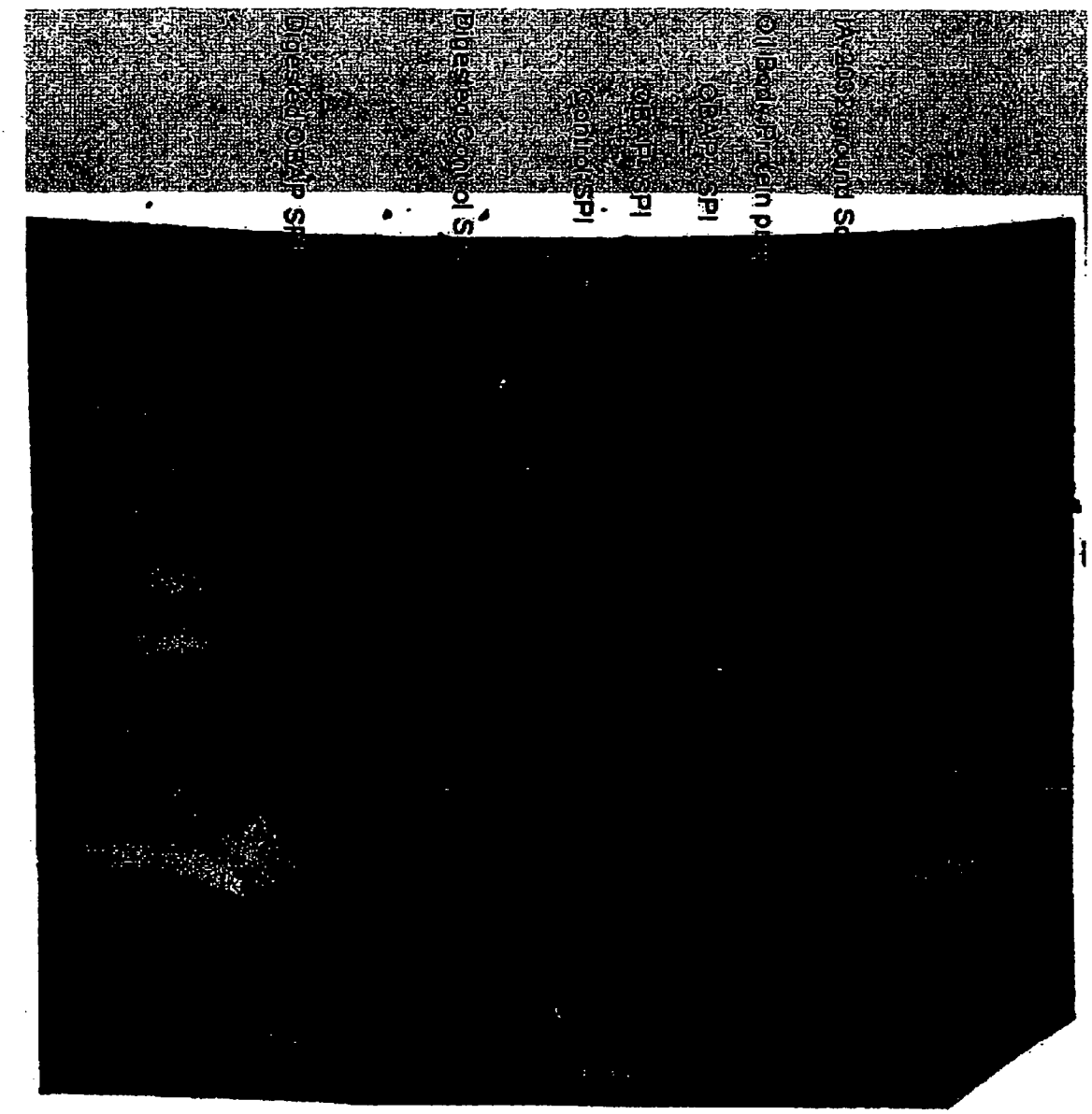
FIG. 13 depicts a gel illustrating the presence or absence of oleosin in the indicated samples.

Samples of pepsin digested SPI (OBAP and control), undigested SPI samples (control, OBAP(−), OBAP(+)), the oil body protein preparation, and a ground soy sample of control soybean IA-2032 were resolved on 18% Tris/glycine gels, and transferred to PVDF membranes. These blots were probed with antisera to oleosin (FIG. 13). This antisera was developed in rabbit using full length oleosin protein that was overexpressed in and purified from *E. coli* as described in QIAexpressionist (QIAGEN Inc., Valencia, Calif.). These blots illustrated that the samples with higher amounts of oleosin produced much higher yields of HMF (Table 6).

Example 5

Effect of Extraction with Ethanol on HMF Yield

To see what extent the high yield of the intermediate fraction came from phospholipids, saponins and isoflavones, these components were extracted from the fraction using 70% ethanol and the fraction was retested for HMF yield. The result was a 50% lower yield. Addition of the extracted fraction to a low yielding fraction (glycinin) helped to improve the yield of HMF of that fraction (80%). These results (see Table 6) suggest that the ability of the HMF polypeptides to resist digestion by proteases may depend in-part on the presence of alcohol extractable components such as saponins, isoflavones and phospholipids. Result from previous examples are also included in Table 6 along with summary explanations. The conclusion from this summary was that oleosins, beta-conglycinins, alcohol extractables (phospholipids, saponins, isoflavones), and basic glycinin subunits contribute to a high yield of HMF which can function as a cholesterol-lowering material. The most important component is lipoprotein (oleosin and associated phospholipid). It is conceived that the cholesterol-lowering properties of a soy protein ingredient containing beta-conglycinins and glycinins can be enhanced by adding lipoproteins from plants (e.g., oleosins with associated phospholipids) or other sources (e.g. egg yolk lipoproteins).

TABLE 6

Comparison of source material and HMF yield

| Material ID | Oleosins and associated phospholipids, isoflavones and saponins | Basic glycinins | Beta-conglycinins | Yield of HMF (%) |
|---|---|---|---|---|
| OBAP-less | − | + | + | 0 |
| Glycinin | − | +++ | − | 5 |
| Glycinin + alcohol extract | + (minus oleosins) | +++ | − | 5 |
| Beta conglycinin null | + | ++ | − | 8 |
| OBAP-rich | + | + | − | 8 |
| Beta-conglycinin | + | − | +++ | 14 |
| Glycinin null | + | − | ++ | 19 |
| Intermediate fraction | + | + | + | 24 |
| Alcohol extracted | + | + | + | 23 |

TABLE 6-continued

Comparison of source material and HMF yield

| Material ID | Oleosins and associated phospholipids, isoflavones and saponins | Basic glycinins | Beta-conglycinins | Yield of HMF (%) |
|---|---|---|---|---|
| intermediate fraction with alcohol extract added back | | | | |
| Alcohol extracted intermediate fraction | + (minus phospholipids, saponins & isoflavones) | + | + | 13 |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the claims.

REFERENCES

The following references, to the extent that they provide exemplary procedural or other details supplementary to those set forth herein, are specifically incorporated herein by reference:

U.S. Pat. No. 4,554,101
U.S. Pat. No. 5,855,892
U.S. Pat. No. 6,171,640
U.S. Pat. No. 6,509,453
Altschul et al., *J. Mol. Biol.*, 215:403-410, 1990.
Anderson et al., *JAMA*, 257:2176-2180, 1987.
Anderson et al., *N. Engl. J. Med.*, 333(5):276-282, 1995.
Arsson, *J. Pharm Sci.*, 79:476-482, 1990.
*Biocomputing: Informatics and Genome Projects*, Smith (Ed.), Academic Press, NY, 1993.
Birren et al., *Genome Analysis*, 1:543-559, 1997.
*BLAST Manual*, Altschul et al., (Eds.), NCBI NLM NIH, Bethesda, Md. 20894.
Bringe and Cheng, *Food Tech.*, 49(5):94-106, 1995.
Bringe, *Adv. Exp. Med. Biol.*, 415:161-181, 1997.
Carillo and Lipman, *J. Applied Math.*, 48:1073, 1988.
Carol and Hamilton, *J. Food Sci.*, 40:18-23, 1975.
Chen et al., *Nutr. Biochem.*, 6:310-313, 1995.
Clauser et al., *Analytical Chemistry*, 71:2871, 1999.
*Computational Molecular Biology*, Lesk (Ed.), Oxford University Press, NY, 1988.
*Computer Analysis of Sequence Data, Part I*, Griffin and Griffin (Eds.), Humana Press, NJ, 1994.
Coulson, *Trends in Biotechnology*, 12: 76-80, 1994.
Devereux et al., *Nucleic Acids Res.*, 12(1):387, 1984.
Field et al., *J. Lipid Research*, 32:1811-1821, 1991.
Gordon et al., *Circulation*, 79:8-15, 1989.
Gurfinkel et al. *J. Agric. Food Chem.*, 50(3):426-430, 2002.
Hidalgo et al., *Gasteroenterology*, 96:736-740, 1989.
Homan and Hamelehle, *J. Lipid Res.*, 39:1197-1209, 1998.
Hori et al., *J. Jpn. Soc. Nutr. Food Sci.*, 52:135-145, 1999.
Huang, *Ann. Rev. Plant Physiol.*, 43:177-200, 1992.
Kyte and Doolittle, *J. Mol. Biol.*, 157:105-132, 1982.
Laemmili, *Nature*, 227:680-685, 1970.
Leber et al., *Yeast*, 10:1421-1428, 1994.
Levy et al., *FASEB J.*, 9:626-635, 1995.
Malone et al, *Electrophoresis*, 22(5):919-932, 2001.
Nagaoka et al., *Biosci. Biotechnol. Biochem.*, 56:1484-1485, 1992.
Nagaoka et al., *J. Nutr.*, 129:1725-1730, 1999.
Nagaoka et al., *J. Nutr.*, 9:725-730, 1999.
Nagoako et al., *J. Nutr.*, 129:1725-1730, 1999.
PCT Appl. WO 00/30602
PCT Appl. WO 00/30663
*Pharmaceutical Dosage Forms*, Leiberman and Lachman (Eds.), Marcel Decker, NY, 1980.
Pieper-Fürst et al., *J. Bacteriol.*, 176:4328-4337, 1994.
Potter, *J. Nutr.*, 125:606S-611S, 1995.
*Remington's Pharmaceutical Sciences*, Mack Publishing Co., Easton, Pa. 1975
Roessler, *J. Phycol.* (London), 24:394-400, 1988.
Samoto et al., *Biosci. Biotechnol. Biochem.*, 62:935-940, 1998.
*Sequence Analysis in Molecular Biology*, von Heinje, Academic Press, 1987.
*Sequence Analysis Primer*, Gribskov and Devereux (Eds.), Stockton Press, NY, 1991.
Shevchenko et al., *Proc. Natl. Acad. Sci. USA*, 93:14440-14445, 1996.
Sugano, et al., *Atherosclerosis*, 72:115-122, 1988.
Taipalensuu et al., *J. Pharmacol. Exp. Ther.*, 299:164-170, 2001.
Topping and Clifton, *Physiol. Rev.*, 81(3):1031-1064, 2001.
Tzen and Huang, *J. Cell Biol.*, 117:327-335, 1992.
Utsumi et al., In: *Food Proteins and Their Applications*, Damodaran and Paraf (Eds.), Marcel Dekker, Inc., NY, 1997.
Werder et al., *Biochemistry*, 40:11643-11650, 2001.
Wu et al., *JAOCS*, 76:285-293, 1999.
Yamauchi and Suetsuna, *Nutr. Biochem.*, 4:450-457, 1993.

The invention claimed is:

1. A composition for lowering serum cholesterol levels comprising:
   (a) glycinin and/or β-conglycinin,
   (b) oleosin, wherein the composition comprises at least 5% oleosin; and
   (c) phospholipid, wherein the phospholipid comprises not less than 2% weight percent of the composition.

2. The composition of claim 1, wherein the glycinin or β-conglycinin is at least partially hydrolyzed by an enzyme or a mixture of enzymes.

3. The composition of claim 1, further comprising β-conglycinin and purified oleosin.

4. The composition of claim 1, wherein the composition comprises from about 5% to about 10% oleosin.

5. The composition of claim 1, wherein the composition comprises greater than about 10% oleosin.

6. The composition of claim 1, wherein the composition comprises about 30% to about 50% oleosin.

7. The composition of claim 1 wherein the phospholipid is selected from the group consisting of lecithin, lyso-lecithin, and lecithin with a modified fatty acid composition.

8. The composition of claim 1, wherein the β-conglycinin is the α' subunit thereof.

9. The composition of claim 1, further comprising more than 40% β-conglycinin.

10. The composition of claim 1, wherein the glycinin is the basic subunit of glycinin.

11. The composition of claim 10, wherein the basic subunit of glycinin is the β-1b subunit.

12. The composition of claim 1, further comprising at least one additive compound, wherein the additive compound is selected from the group consisting of a saponin, a phytoestrogen, and a carbohydrate substantially resistant to digestion.

13. The composition of claim 12, wherein the carbohydrate is selected from the group consisting of high amylose starch, oligofructose, and soy cotyledon fiber.

14. The composition of claim 12, wherein the saponin is selected from the group consisting of soy saponin A, saponin B, saponin E, sapogenol A, sapogenol B, and sapogenol E.

15. The composition of claim 12, wherein the phytoestrogen comprises an isoflavone.

16. The composition of claim 15, wherein the isoflavone is selected from the group consisting of genistein, diadzein, equol, biochanin A, formononetin, and their respective naturally occurring glucosides and glucoside conjugates.

17. A method of preparing a foodstuff, comprising the steps of:
   (a) obtaining a selected foodstuff; and
   (b) adding the composition of claim 1 to the foodstuff, wherein the consumption of an effective amount of the foodstuff lowers the serum cholesterol levels of a subject in need thereof.

18. The method of claim 17, further comprising adding at least one compound selected from the group consisting of a saponin, a phytoestrogen, and a carbohydrate substantially resistant to digestion.

19. The method of claim 17, wherein the foodstuff lacks oleosin prior to the step of adding.

20. The method of claim 17, wherein the foodstuff comprises oleosin prior to the step of adding.

21. The method of claim 17, wherein the foodstuff is soy-based.

22. The method of claim 21, wherein the foodstuff is selected from the group consisting of soy flour, soy grit, soy meal, soy flakes, soy milk powder, soy protein concentrate, soy protein isolate and isolated soy polypeptide.

23. The method of claim 22, wherein the soy protein isolate is a high molecular weight fraction of a soy material treated with a protease.

24. The method of claim 22, wherein the isolated soy polypeptide comprises β-conglycinin.

25. The method of claim 12, wherein the isolated soy polypeptide is glycinin.

26. A method for lowering serum cholesterol levels comprising the steps of:
   (a) adding the composition of claim 1 to a selected foodstuff; and
   (b) providing the foodstuff to a subject in need thereof in a quantity sufficient to lower serum cholesterol levels.

27. The method of claim 26, further comprising adding at least one compound to the foodstuff selected from the group consisting of a saponin, a phytoestrogen, and a carbohydrate substantially resistant to digestion.

28. The method of claim 26, wherein the foodstuff is a soy-based.

29. The method of claim 26, wherein the foodstuff lacks oleosin prior to the step of adding.

30. The method of claim 26, wherein the foodstuff comprises oleosin prior to the step of adding.

31. The method of claim 30, wherein the foodstuff is selected from the group consisting of soy flour, soy grit, soy meal, soy flakes, soy milk powder, soy protein concentrate, soy protein isolate and isolated soy polypeptide.

32. The method of claim 31, wherein the soy protein isolate is a high molecular weight fraction of a soy material treated with a protease.

33. The method of claim 31 wherein the isolated soy polypeptide comprises β-conglycinin.

34. The method of claim 31 wherein the isolated soy polypeptide is glycinin.

* * * * *

UNITED STATES PATENT AND TRADEMARK OFFICE
CERTIFICATE OF CORRECTION

PATENT NO. : 7,541,329 B2  
APPLICATION NO. : 10/511669  
DATED : June 2, 2009  
INVENTOR(S) : Bringe et al.

Page 1 of 1

It is certified that error appears in the above-identified patent and that said Letters Patent is hereby corrected as shown below:

In claim 25, column 50, line 20, delete "claim 12" and insert --claim 22--.

Signed and Sealed this

Twenty-third Day of November, 2010

David J. Kappos  
*Director of the United States Patent and Trademark Office*